United States Patent
Abdou

(10) Patent No.: US 9,375,239 B2
(45) Date of Patent: Jun. 28, 2016

(54) SPINAL FIXATION DEVICES AND METHODS OF USE

(71) Applicant: Samy Abdou, San Diego, CA (US)

(72) Inventor: Samy Abdou, San Diego, CA (US)

(*) Notice: Subject to any disclaimer, the term of this patent is extended or adjusted under 35 U.S.C. 154(b) by 0 days.

(21) Appl. No.: 14/451,281

(22) Filed: Aug. 4, 2014

(65) Prior Publication Data

US 2015/0032163 A1 Jan. 29, 2015

Related U.S. Application Data

(63) Continuation of application No. 12/940,960, filed on Nov. 5, 2010, now Pat. No. 8,795,335.

(60) Provisional application No. 61/280,666, filed on Nov. 6, 2009.

(51) Int. Cl.
*A61B 17/88* (2006.01)
*A61B 17/70* (2006.01)
*A61F 2/44* (2006.01)

(52) U.S. Cl.
CPC ......... *A61B 17/7068* (2013.01); *A61B 17/7065* (2013.01); *A61F 2/4455* (2013.01)

(58) Field of Classification Search
CPC .................................................. A61B 17/7065
USPC .................................... 606/246–253, 279, 71
See application file for complete search history.

(56) References Cited

U.S. PATENT DOCUMENTS

| | | | |
|---|---|---|---|
| 3,090,386 A | 5/1963 | Babcock | |
| 4,037,592 A | 7/1977 | Kronner | |
| 4,569,662 A | 2/1986 | Dragan | |
| 4,580,563 A | 4/1986 | Gross | |
| 4,611,582 A | 9/1986 | Duff | |
| 4,722,331 A | 2/1988 | Fox | |
| 4,899,761 A | 2/1990 | Brown et al. | |
| 5,011,484 A | 4/1991 | Breard | |
| 5,254,118 A | 10/1993 | Mirkovic | |

(Continued)

FOREIGN PATENT DOCUMENTS

| | | |
|---|---|---|
| DE | 10035182 | 2/2002 |
| EP | 77159 | 4/1983 |

(Continued)

OTHER PUBLICATIONS

Korkala, O., et al., Reduction and Fixation of Late Diagnosed Lower Cervical Spine Dislocations Using the Daab Plate: A Report of Two Cases, Arch Orthop Trauma Surg 1984;103(5):353-5.

(Continued)

*Primary Examiner* — Ellen C Hammond
*Assistant Examiner* — Stuart S Bray
(74) *Attorney, Agent, or Firm* — Gazdzinski & Associates, PC

(57) ABSTRACT

Disclosed is an orthopedic implant and methods of implantation for fixing adjacent bones. In an embodiment, the implant includes a locking mechanism that is adapted to be advanced by a locking instrument, wherein advancement of the locking mechanism in a first direction produces rotation of a first rigid abutment surface from a first orientation to a second orientation, and continued advancement of the locking mechanism produces advancement of the first rigid abutment surface towards a second rigid abutment surface and placement of a compressive load onto and sufficient to immobilize the implant relative to the first bony surface and the second bony surface.

51 Claims, 38 Drawing Sheets

(56) References Cited

U.S. PATENT DOCUMENTS

| | | |
|---|---|---|
| 5,330,468 A | 7/1994 | Burkhart |
| 5,334,205 A | 8/1994 | Cain |
| 5,496,318 A | 3/1996 | Howland et al. |
| 5,569,248 A | 10/1996 | Mathews |
| 5,645,599 A | 7/1997 | Samani |
| 5,928,139 A | 7/1999 | Koros et al. |
| 5,976,146 A | 11/1999 | Ogawa et al. |
| 6,039,761 A | 3/2000 | Li et al. |
| 6,048,342 A | 4/2000 | Zucherman et al. |
| 6,090,113 A | 7/2000 | Le Couedic et al. |
| 6,123,707 A | 9/2000 | Wagner |
| 6,159,244 A | 12/2000 | Suddaby |
| 6,193,757 B1 | 2/2001 | Foley et al. |
| 6,312,431 B1 | 11/2001 | Asfora |
| 6,319,002 B1 | 11/2001 | Pond |
| 6,319,257 B1 | 11/2001 | Carignan et al. |
| 6,355,038 B1 | 3/2002 | Pisharodi |
| 6,375,681 B1 | 4/2002 | Truscott |
| 6,419,676 B1 | 7/2002 | Zucherman et al. |
| 6,428,576 B1 | 8/2002 | Haldimann |
| 6,440,133 B1 | 8/2002 | Beale et al. |
| 6,451,019 B1 | 9/2002 | Zucherman et al. |
| 6,478,800 B1 | 11/2002 | Fraser et al. |
| 6,508,839 B1 | 1/2003 | Lambrecht et al. |
| 6,530,929 B1 | 3/2003 | Justis et al. |
| 6,558,386 B1 | 5/2003 | Cragg |
| 6,558,390 B2 | 5/2003 | Cragg |
| 6,582,433 B2 | 6/2003 | Yun |
| 6,599,294 B2 | 7/2003 | Fuss et al. |
| 6,599,295 B1 | 7/2003 | Tornier et al. |
| 6,699,247 B2 | 3/2004 | Zucherman et al. |
| 6,716,212 B1 | 4/2004 | Pickens |
| 6,730,126 B2 | 5/2004 | Boehm, Jr. et al. |
| 6,739,068 B1 | 5/2004 | Rinner |
| 6,740,087 B2 | 5/2004 | Knox |
| 6,740,090 B1 | 5/2004 | Cragg et al. |
| 6,746,449 B2 | 6/2004 | Jones et al. |
| 6,749,614 B2 | 6/2004 | Teitelbaum et al. |
| 6,755,841 B2 | 6/2004 | Fraser et al. |
| 6,761,720 B1 | 7/2004 | Senegas |
| 6,783,547 B2 | 8/2004 | Castro |
| 6,790,210 B1 | 9/2004 | Cragg et al. |
| 6,805,697 B1 | 10/2004 | Helm et al. |
| 6,821,277 B2 | 11/2004 | Teitelbaum |
| 6,875,211 B2 | 4/2005 | Nichols et al. |
| 6,899,716 B2 | 5/2005 | Cragg |
| 6,921,403 B2 | 7/2005 | Cragg et al. |
| 7,008,422 B2 | 3/2006 | Foley et al. |
| 7,011,660 B2 | 3/2006 | Sherman et al. |
| 7,014,633 B2 | 3/2006 | Cragg |
| 7,048,736 B2 | 5/2006 | Robinson et al. |
| 7,060,066 B2 | 6/2006 | Zhao et al. |
| 7,070,598 B2 | 7/2006 | Lim et al. |
| 7,087,058 B2 | 8/2006 | Cragg |
| 7,087,083 B2 | 8/2006 | Pasquet et al. |
| 7,118,579 B2 | 10/2006 | Michelson |
| 7,118,580 B1 | 10/2006 | Beyersdorff et al. |
| 7,153,281 B2 | 12/2006 | Homes |
| 7,160,300 B2 | 1/2007 | Jackson |
| 7,201,751 B2 | 4/2007 | Zucherman et al. |
| 7,232,463 B2 | 6/2007 | Falahee |
| 7,338,527 B2 | 3/2008 | Blatt et al. |
| 7,445,637 B2 * | 11/2008 | Taylor ............... A61B 17/7062 606/249 |
| 7,455,685 B2 | 11/2008 | Justis |
| 7,572,276 B2 | 8/2009 | Lim et al. |
| 7,585,316 B2 | 9/2009 | Trieu |
| 7,753,938 B2 | 7/2010 | Aschmann et al. |
| 7,935,147 B2 * | 5/2011 | Wales ............... A61B 17/0057 623/17.16 |
| 8,021,393 B2 * | 9/2011 | Seifert ............... A61B 17/3468 606/248 |
| 8,075,593 B2 | 12/2011 | Hess |
| 8,142,479 B2 | 3/2012 | Hess |
| 8,308,804 B2 * | 11/2012 | Krueger ............... A61F 2/442 623/17.11 |
| 8,382,801 B2 | 2/2013 | Lamborne et al. |
| 8,906,092 B2 * | 12/2014 | Abdou ............... A61B 17/7065 606/248 |
| 8,940,052 B2 * | 1/2015 | Lechmann ............ A61F 2/442 606/246 |
| 2001/0012938 A1 | 8/2001 | Zucherman |
| 2001/0021850 A1 | 9/2001 | Zucherman |
| 2001/0031965 A1 | 10/2001 | Zucherman et al. |
| 2002/0045904 A1 | 4/2002 | Fuss et al. |
| 2002/0049444 A1 | 4/2002 | Knox |
| 2002/0161368 A1 | 10/2002 | Foley et al. |
| 2003/0018389 A1 | 1/2003 | Castro et al. |
| 2003/0074005 A1 | 4/2003 | Roth et al. |
| 2003/0187436 A1 | 10/2003 | Bolger et al. |
| 2003/0229347 A1 | 12/2003 | Sherman et al. |
| 2003/0236472 A1 | 12/2003 | Van Hoeck et al. |
| 2004/0030346 A1 * | 2/2004 | Frey ............... A61B 17/1604 606/99 |
| 2004/0044412 A1 * | 3/2004 | Lambrecht ............ A61B 5/1076 623/17.16 |
| 2004/0138671 A1 | 7/2004 | Zander et al. |
| 2004/0167625 A1 | 8/2004 | Beyar et al. |
| 2005/0021029 A1 | 1/2005 | Trieu et al. |
| 2005/0021031 A1 | 1/2005 | Foley et al. |
| 2005/0021040 A1 | 1/2005 | Bertagnoli |
| 2005/0055031 A1 | 3/2005 | Lim et al. |
| 2005/0085813 A1 | 4/2005 | Spitler et al. |
| 2005/0119747 A1 | 6/2005 | Fabris et al. |
| 2005/0131421 A1 | 6/2005 | Anderson et al. |
| 2005/0154389 A1 | 7/2005 | Selover et al. |
| 2005/0165398 A1 | 7/2005 | Reiley |
| 2005/0171540 A1 | 8/2005 | Lim et al. |
| 2005/0177163 A1 | 8/2005 | Abdou |
| 2005/0192589 A1 | 9/2005 | Raymond |
| 2005/0197660 A1 | 9/2005 | Haid et al. |
| 2005/0203512 A1 | 9/2005 | Hawkins et al. |
| 2005/0203533 A1 | 9/2005 | Ferguson et al. |
| 2005/0209694 A1 | 9/2005 | Loeb |
| 2005/0215999 A1 | 9/2005 | Birkmeyer et al. |
| 2005/0234449 A1 | 10/2005 | Aferzon |
| 2005/0234451 A1 | 10/2005 | Markworth |
| 2005/0245928 A1 | 11/2005 | Colleran |
| 2005/0261768 A1 | 11/2005 | Trieu |
| 2005/0273120 A1 | 12/2005 | Abdou |
| 2005/0288669 A1 | 12/2005 | Abdou et al. |
| 2006/0015181 A1 | 1/2006 | Elberg |
| 2006/0052870 A1 | 3/2006 | Ferree |
| 2006/0074488 A1 | 4/2006 | Abdou |
| 2006/0084986 A1 | 4/2006 | Grinberg et al. |
| 2006/0084988 A1 | 4/2006 | Kim |
| 2006/0111728 A1 | 5/2006 | Abdou |
| 2006/0142761 A1 | 6/2006 | Landry et al. |
| 2006/0149238 A1 | 7/2006 | Sherman et al. |
| 2006/0149278 A1 | 7/2006 | Abdou |
| 2006/0167454 A1 | 7/2006 | Ludwig et al. |
| 2006/0184247 A1 | 8/2006 | Edidin et al. |
| 2006/0195102 A1 | 8/2006 | Malandain |
| 2006/0217710 A1 | 9/2006 | Abdou |
| 2006/0229614 A1 | 10/2006 | Foley et al. |
| 2006/0229615 A1 | 10/2006 | Abdou |
| 2006/0247630 A1 | 11/2006 | Lott et al. |
| 2006/0247634 A1 | 11/2006 | Warner et al. |
| 2006/0247640 A1 | 11/2006 | Blackwell et al. |
| 2006/0264942 A1 | 11/2006 | Lim et al. |
| 2006/0276803 A1 | 12/2006 | Salerni |
| 2006/0293662 A1 | 12/2006 | Boyer, II et al. |
| 2007/0032790 A1 | 2/2007 | Aschmann et al. |
| 2007/0093823 A1 | 4/2007 | Booth et al. |
| 2007/0093828 A1 | 4/2007 | Abdou |
| 2007/0106383 A1 | 5/2007 | Abdou |
| 2007/0123884 A1 | 5/2007 | Abdou |
| 2007/0151116 A1 | 7/2007 | Malandain |
| 2007/0162000 A1 | 7/2007 | Perkins |
| 2007/0162001 A1 | 7/2007 | Chin et al. |
| 2007/0162005 A1 | 7/2007 | Peterson et al. |
| 2007/0179500 A1 | 8/2007 | Chin et al. |
| 2007/0225807 A1 | 9/2007 | Phan et al. |

(56) References Cited

U.S. PATENT DOCUMENTS

| | | |
|---|---|---|
| 2007/0233082 A1 | 10/2007 | Chin et al. |
| 2007/0233084 A1 | 10/2007 | Betz et al. |
| 2007/0270840 A1 | 11/2007 | Chin et al. |
| 2008/0027438 A1* | 1/2008 | Abdou ............... A61B 17/7065 606/249 |
| 2008/0177391 A1 | 7/2008 | Mitchell et al. |
| 2008/0183211 A1* | 7/2008 | Lamborne .......... A61B 17/7068 606/249 |
| 2008/0183218 A1 | 7/2008 | Mueller et al. |
| 2009/0105761 A1* | 4/2009 | Robie ................ A61B 17/1671 606/246 |
| 2009/0290316 A1 | 11/2009 | Kariya |
| 2010/0016906 A1* | 1/2010 | Abdou .................. A61F 2/4611 606/86 R |
| 2010/0069929 A1 | 3/2010 | Abdou |
| 2010/0106250 A1 | 4/2010 | Abdou |
| 2010/0234889 A1 | 9/2010 | Hess |
| 2011/0054531 A1* | 3/2011 | Lamborne .......... A61B 17/7068 606/249 |
| 2011/0166600 A1* | 7/2011 | Lamborne .......... A61B 17/7068 606/249 |
| 2012/0029565 A1 | 2/2012 | Seifert et al. |
| 2012/0078301 A1 | 3/2012 | Hess |
| 2012/0089184 A1 | 4/2012 | Yeh |
| 2012/0101528 A1 | 4/2012 | Souza et al. |
| 2012/0150229 A1 | 6/2012 | Hess |
| 2012/0209271 A1 | 8/2012 | Cohen et al. |
| 2012/0232592 A1 | 9/2012 | Massoudi |
| 2012/0253393 A1 | 10/2012 | Fiorella |
| 2012/0253396 A1 | 10/2012 | Stern et al. |
| 2013/0060284 A1 | 3/2013 | Abdou |
| 2013/0066374 A1 | 3/2013 | Galley et al. |
| 2013/0103089 A1 | 4/2013 | Gordon et al. |
| 2013/0144339 A1 | 6/2013 | Choi et al. |
| 2013/0144340 A1 | 6/2013 | Sheffer et al. |
| 2013/0150886 A1 | 6/2013 | Altarac et al. |
| 2013/0172932 A1 | 7/2013 | Altarac et al. |
| 2013/0172933 A1 | 7/2013 | Altarac et al. |

FOREIGN PATENT DOCUMENTS

| | | |
|---|---|---|
| EP | 0611116 | 8/2004 |
| EP | 1442715 | 8/2004 |
| WO | WO 2005-077288 | 8/2005 |
| WO | WO 2006-041963 | 4/2006 |
| WO | WO 2006-058221 | 6/2006 |
| WO | WO 2007-041648 | 4/2007 |
| WO | WO 2007-044705 | 4/2007 |
| WO | WO 2008-013960 | 1/2008 |

OTHER PUBLICATIONS

Nardi, Pier V, Md, et al., Aperius PercLID Stand Alone Interspinous System for the Treatment of Degenerative Lumbar Stenosis, J Spinal Disord Tech, May 2010, pp. 203-207 vol. 23—No. 10.

Neo M, et al., Spinous process plate fixation as a salvage operation for failed anterior cervical fusion, J Neurosurg Spine Jan. 2006; 4(1):78-81.

Ozgur, B. et al., Extreme Lateral Interbody Fusion (XLIF): a novel surgical technique for anterior lumbar interbody fusion, Spine J. Jul.-Aug. 2006; 6(4):435-43.

Rapoff, A.J. et al., Biomechanical Comparison of Posterior Lumbar Interbody Fusion Cages, Spine (Phila Pa 1976) Oct. 15, 1997;22(20):2375-9.

Thomsen, K., et al., 1997 Volvo Award winner in Clinical Studies, The Effect of Pedicle Screw Instrumentation on Functional Outcome and Fusion Rates in Posterolateral Lumbar Spinal Fusion: A Prospective, Randomized Clinical Study, Spine (Phila Pa 1976) Dec. 15, 1997;22(24):2813-22.

Voor, M.J., et al., Biomechanical Evaluation of Posterior and Anterior Lumbar Interbody Fusion Techniques, J Spinal Disord Aug. 1998;11(4):328-34.

Wang, J., et al., SPIRE spinous process stabilization plate: biomechanical evaluation of a novel technology. Invited submission from the Joint Section Meeting on Disorders of the Spine and Peripheral Nerves, Mar. 2005, J Neurosurg Spine Feb. 2006;4(2):160-4.

Balderston, R.A., et al., Technique for Achievement and Maintenance of Reduction for Severe Spondylolisthesis Using Spinous Process Traction Wiring and External Fixation of the Pelvis, Spine May 1985 :10(4):376-82.

Bostman, O., et al., Posterior spinal fusion using internal fixation with the Daab plate, Acta Orthop Scand Jun. 1984;55(3):310-4.

Deguchi, M., et al., Biomechanical Comparison of Spondylolysis Fixation Techniques, Spine (Phila Pa 1976) Feb. 15, 1999;24(4):328-33.

Denis, F. The Three Column Spine and Its Significance in the Classification of Acute Thoracolumbar Spinal Injuries, Spine Nov.-Dec. 1983; 8(8):817-831.

Derwent WPI Acc No. 2002-155861/200221 for German Patent No. DE 10035182 (item FV).

Fischgrund, J.S., et al., 1997 Volvo Award Winner in Clinical Studies, Degenerative Lumbar Spondylolisthesis With Spinal Stenosis: A Prospective, Randomized Study Comparing Decompressive Laminectomy and Arthrodesis With and Without Spinal Instrumentation, Spine (Phila Pa 1976) Dec. 15, 1997;22(24):2807-12.

Heggeness, M.H., et al,, Translaminar Facet Joint Screw Fixation for Lumbar and Lumbosacral Fusion; A Clinical and Biomechanical Study, Spine (Phila Pa 1976) Jun. 1991;16(6 Suppl):S266-9.

* cited by examiner

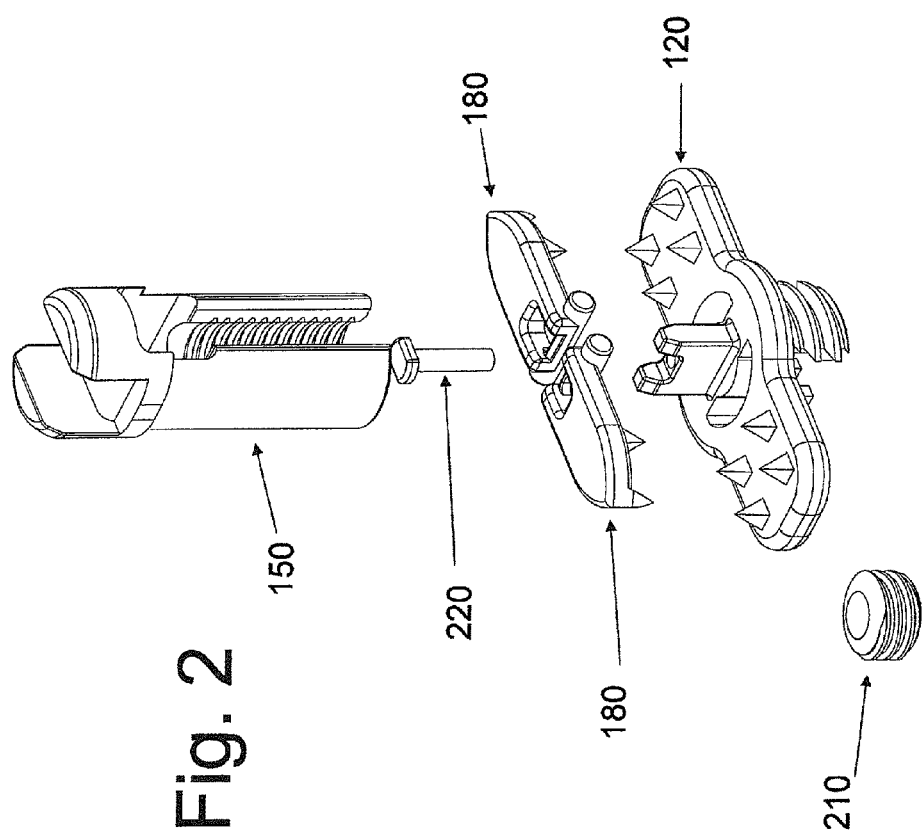

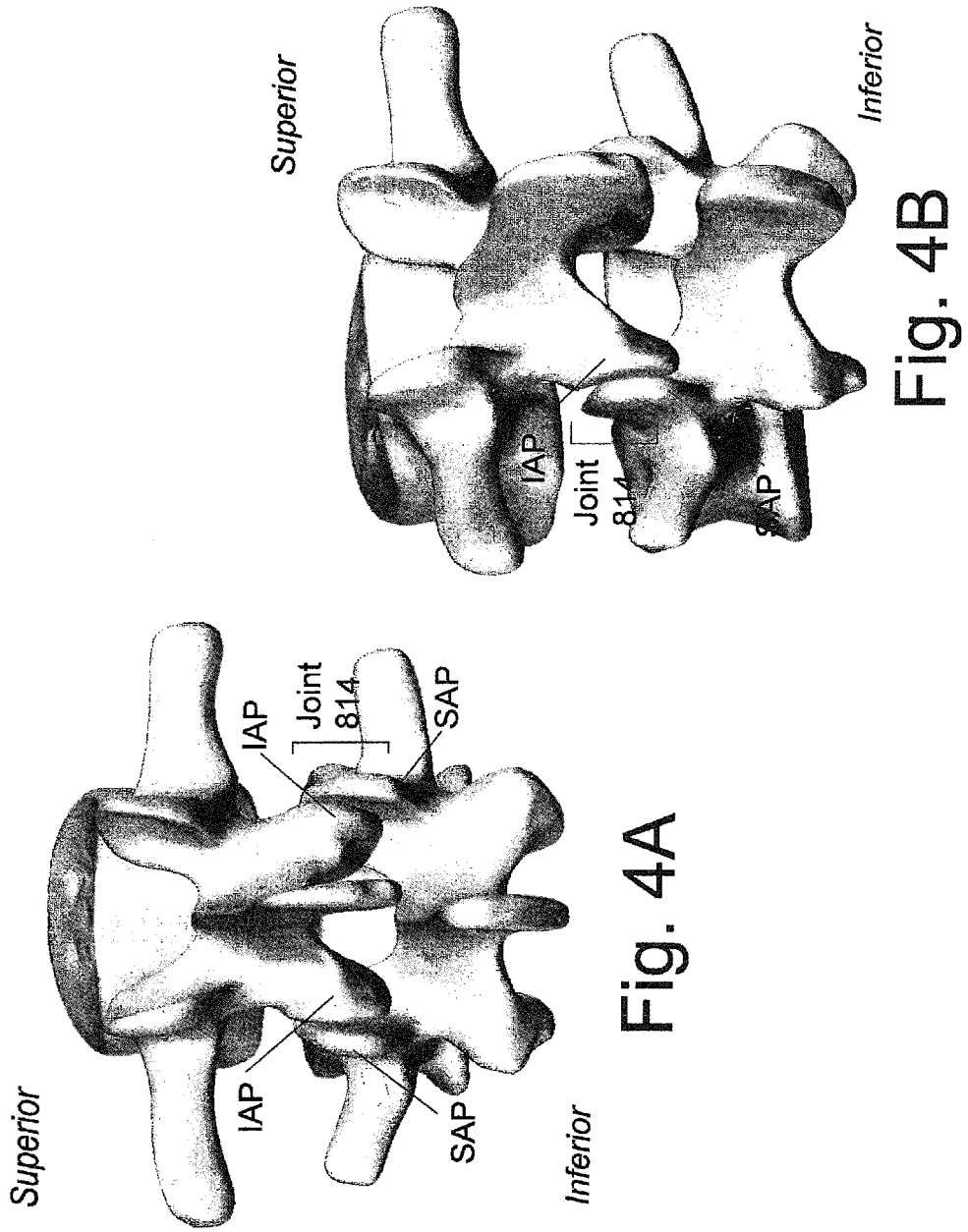

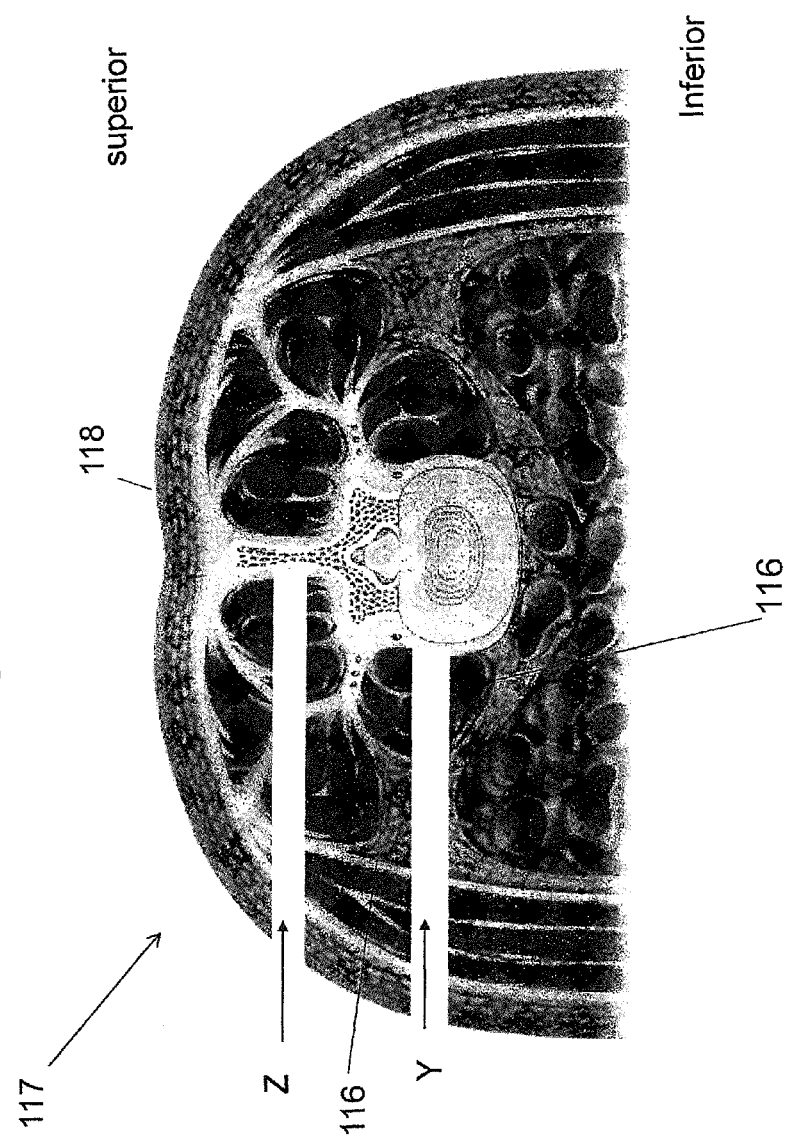

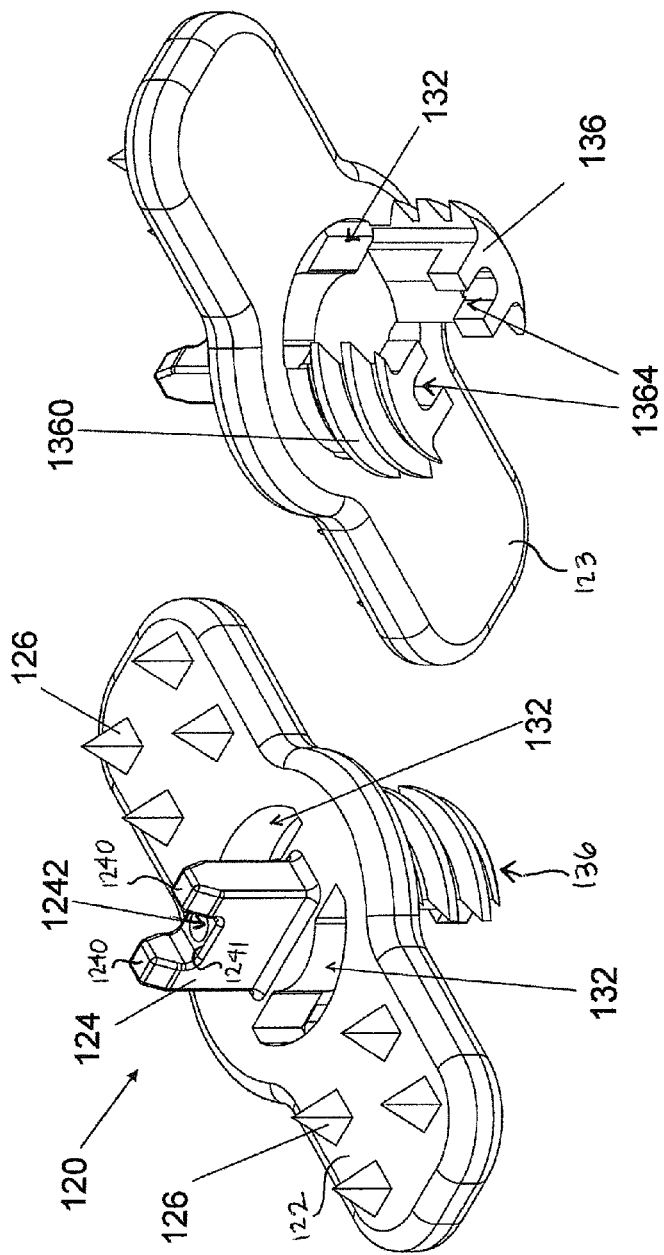

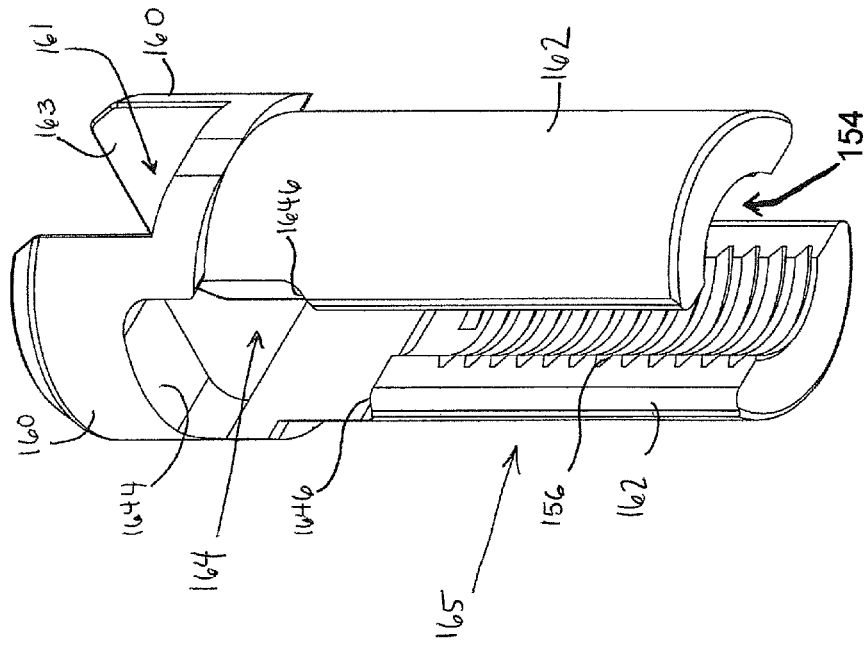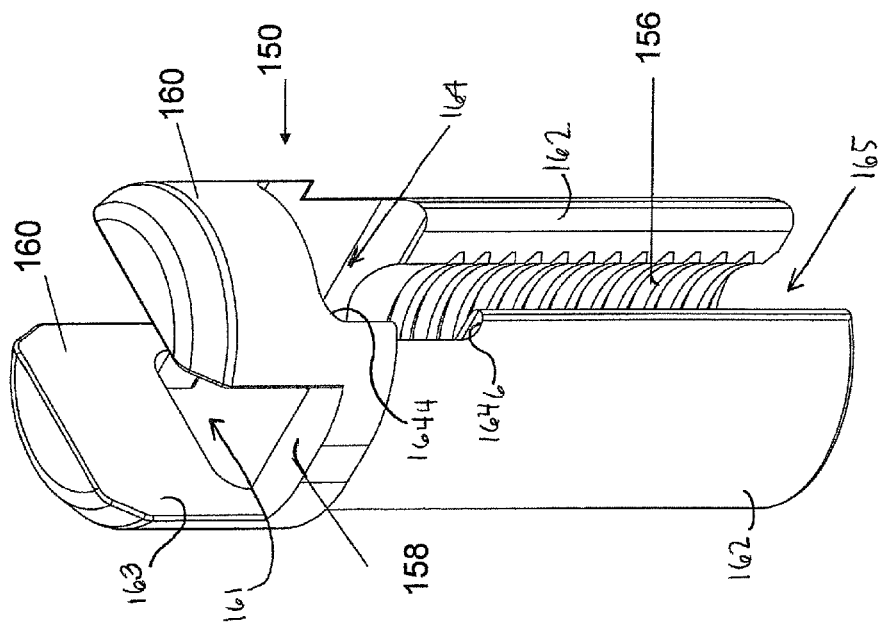

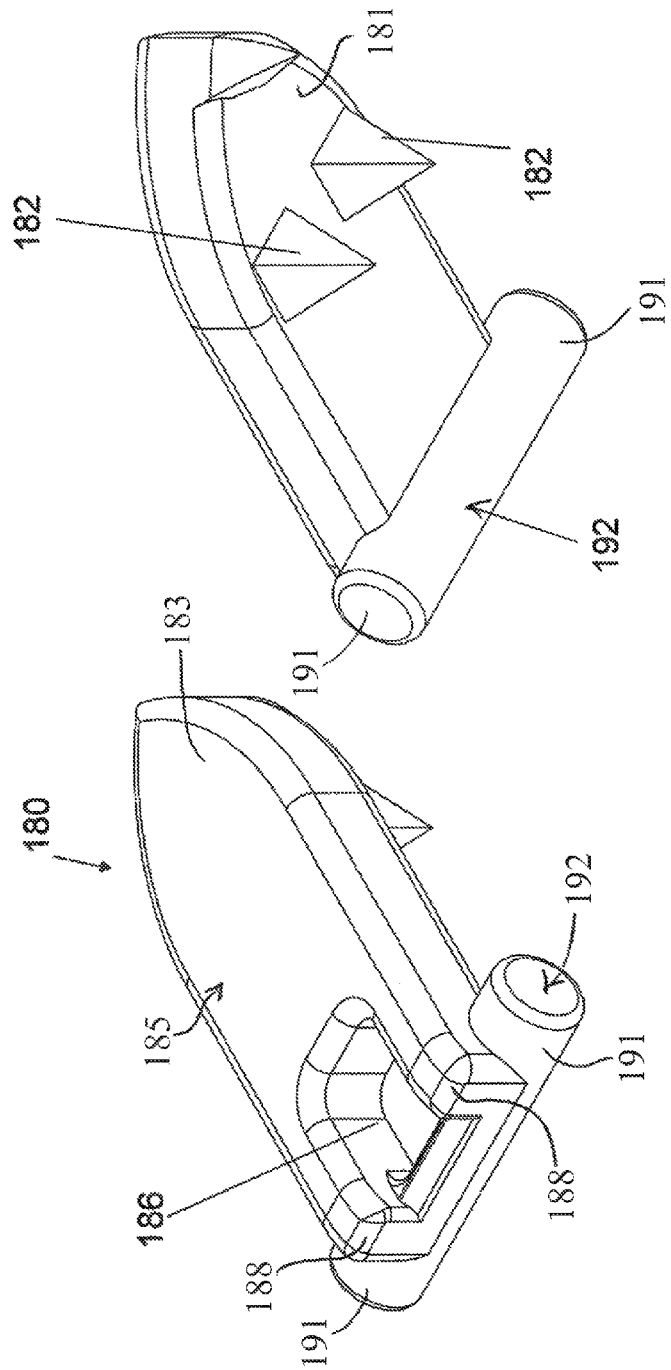

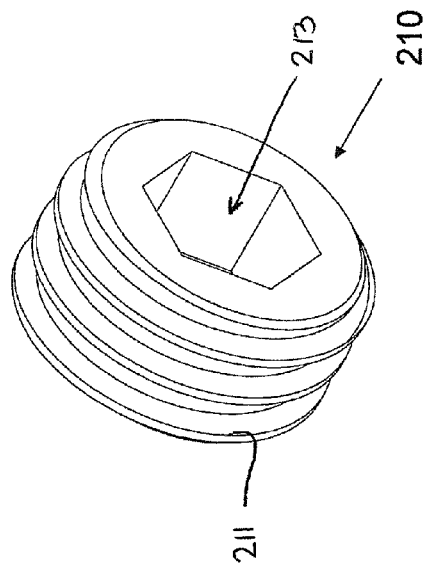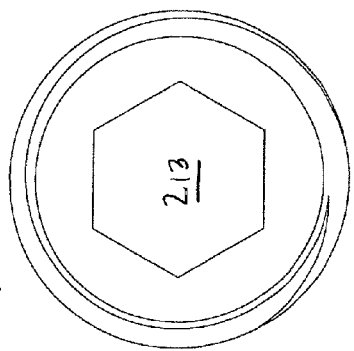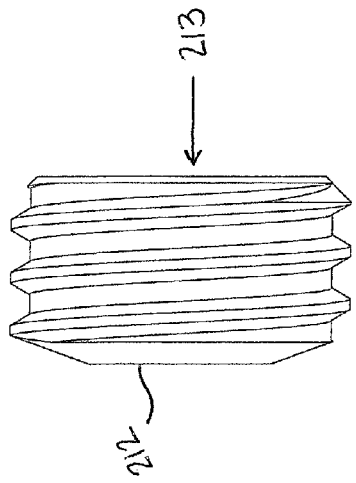

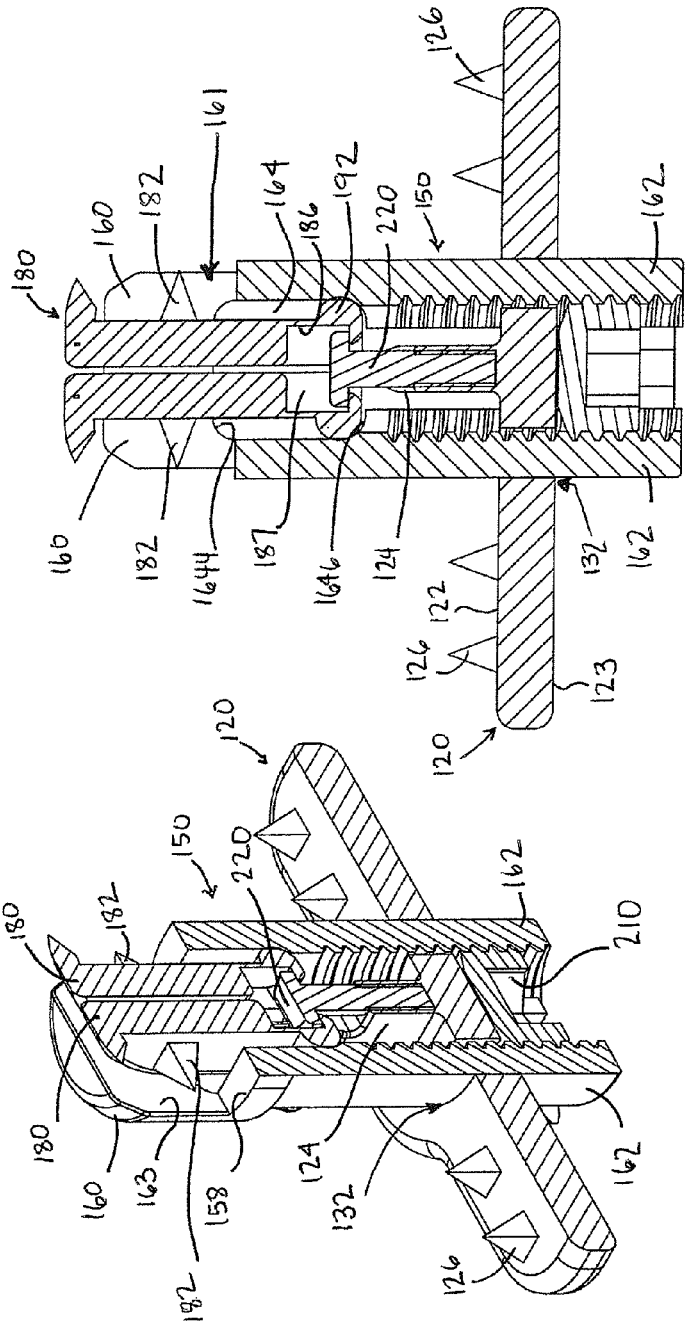

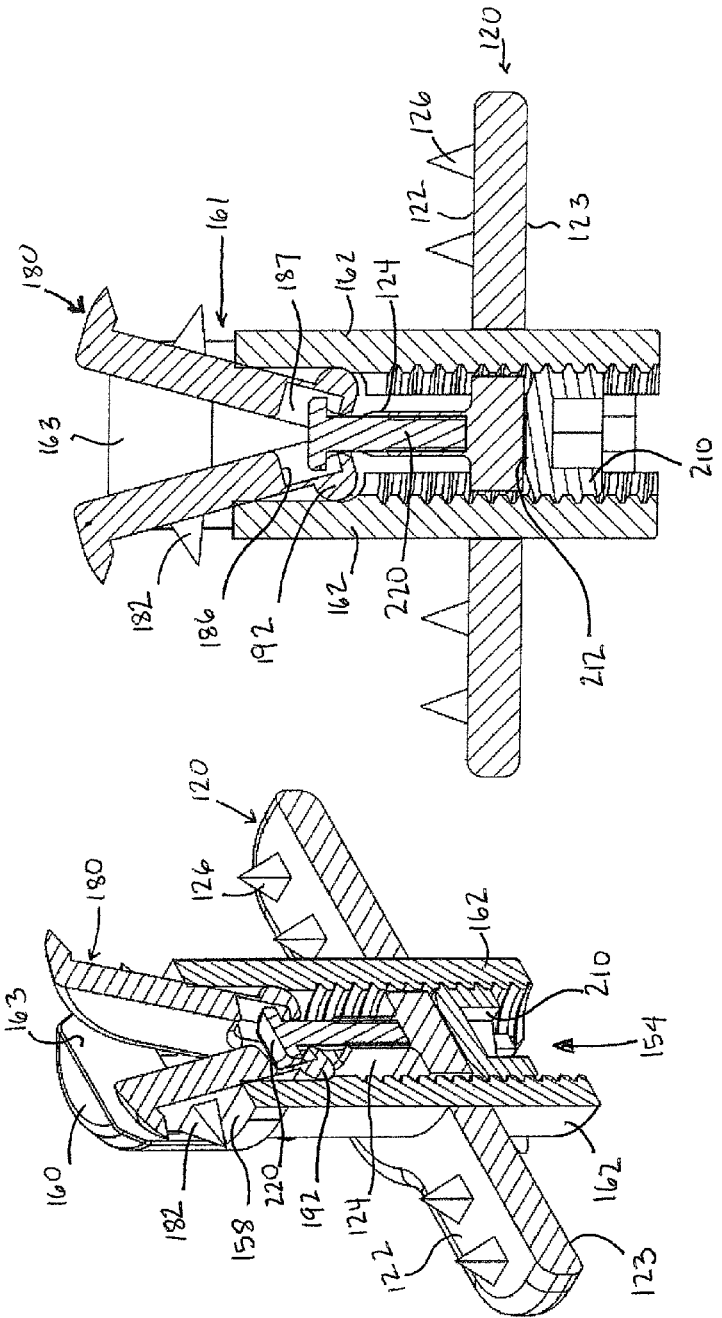

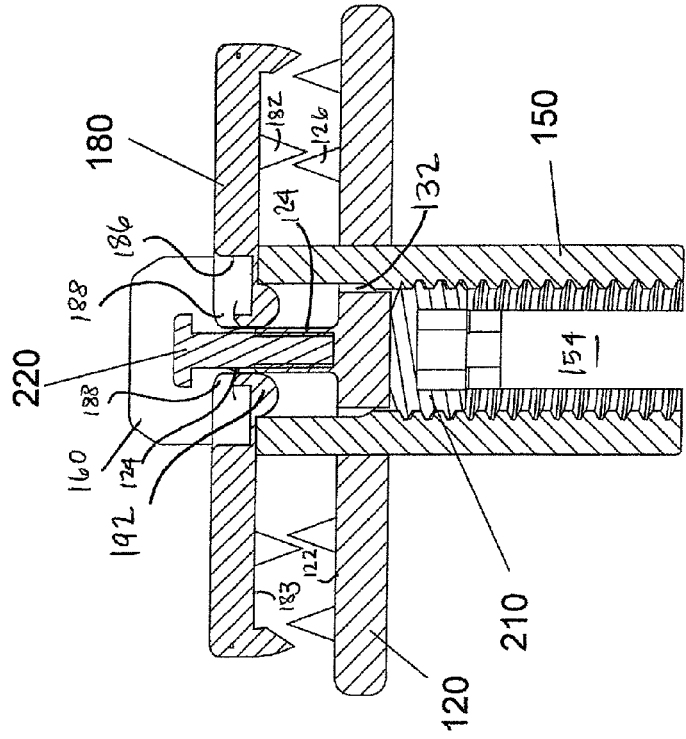
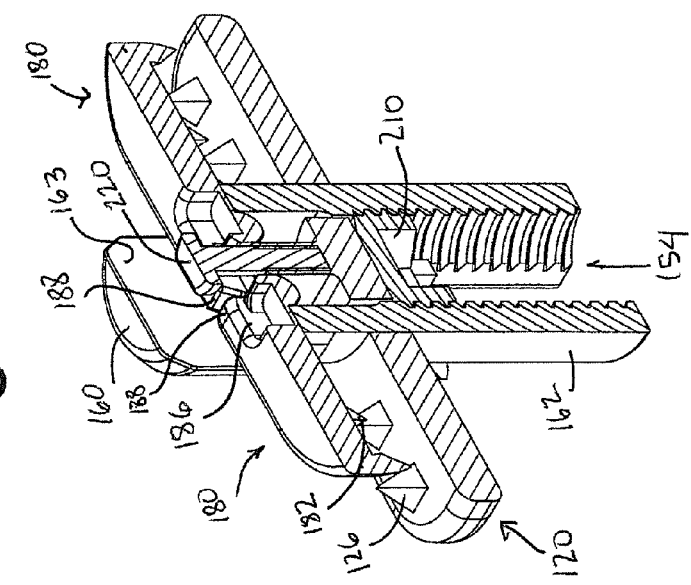

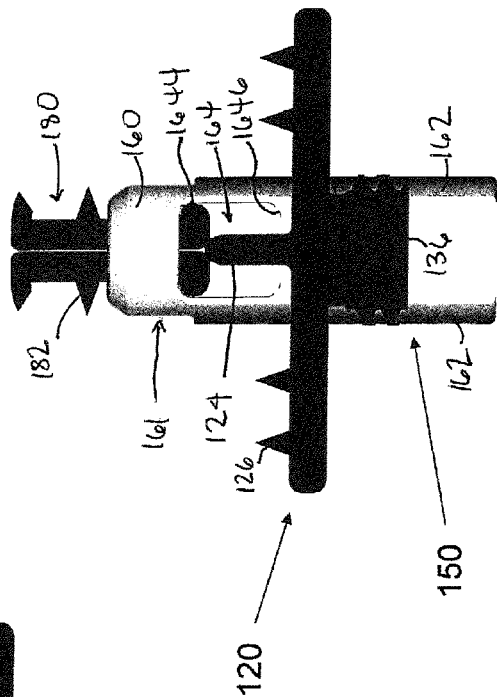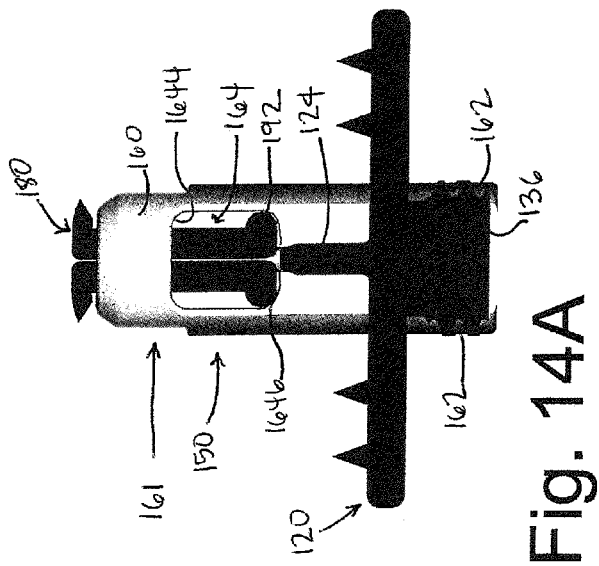

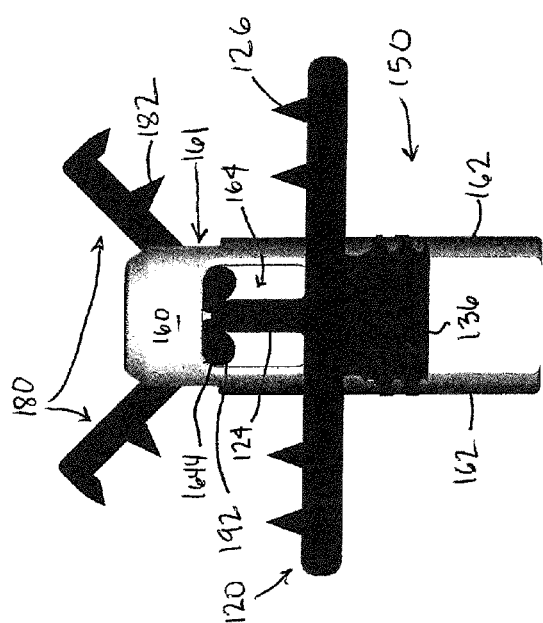
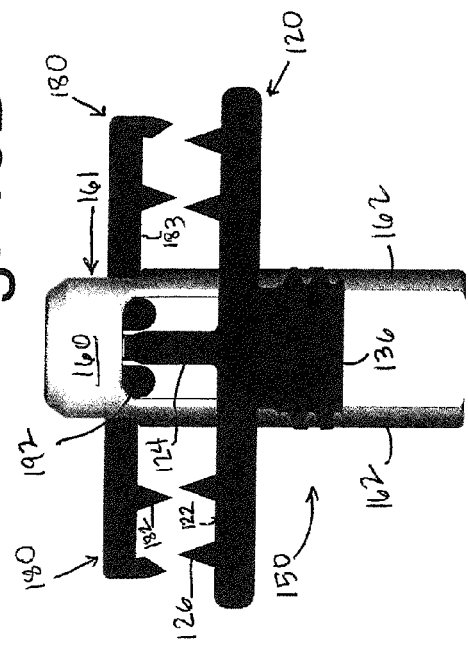

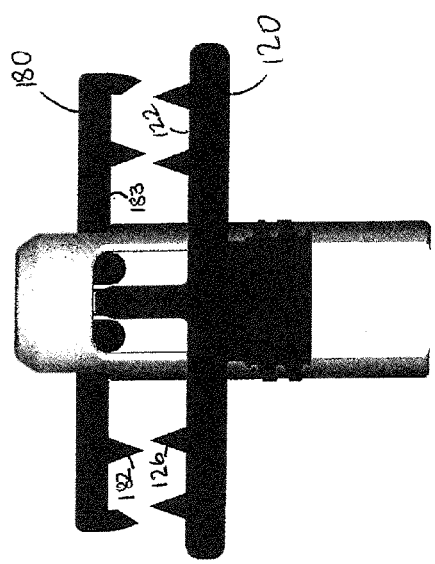
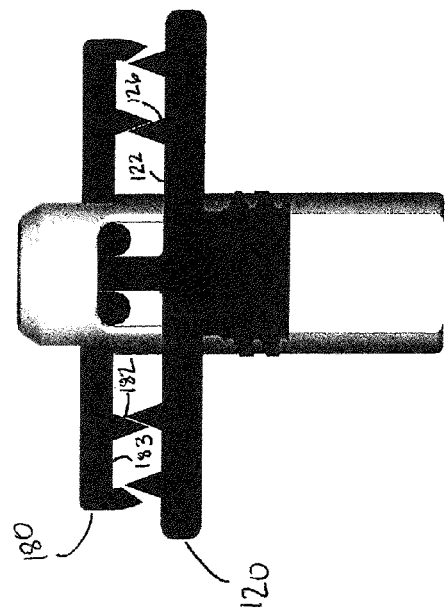

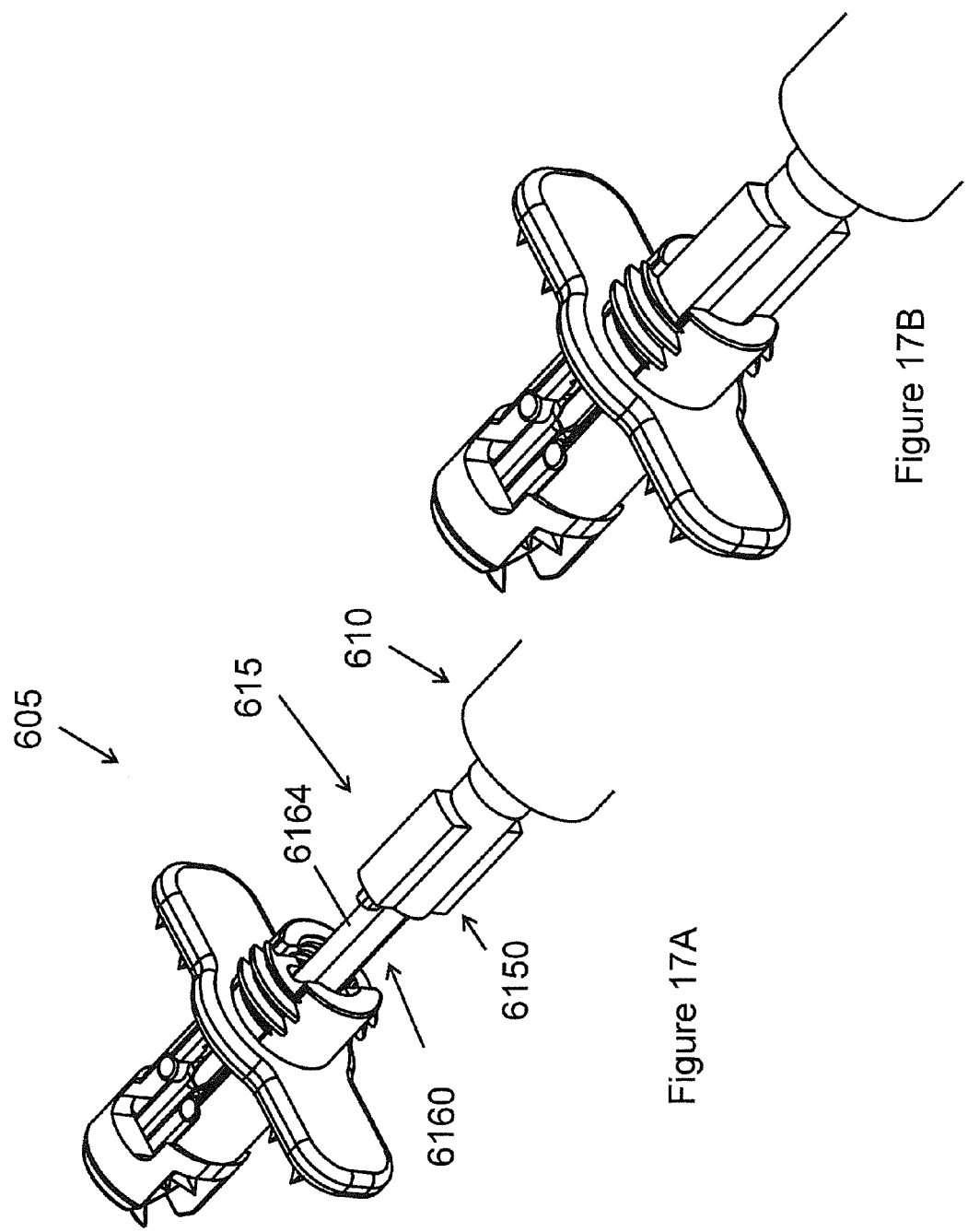

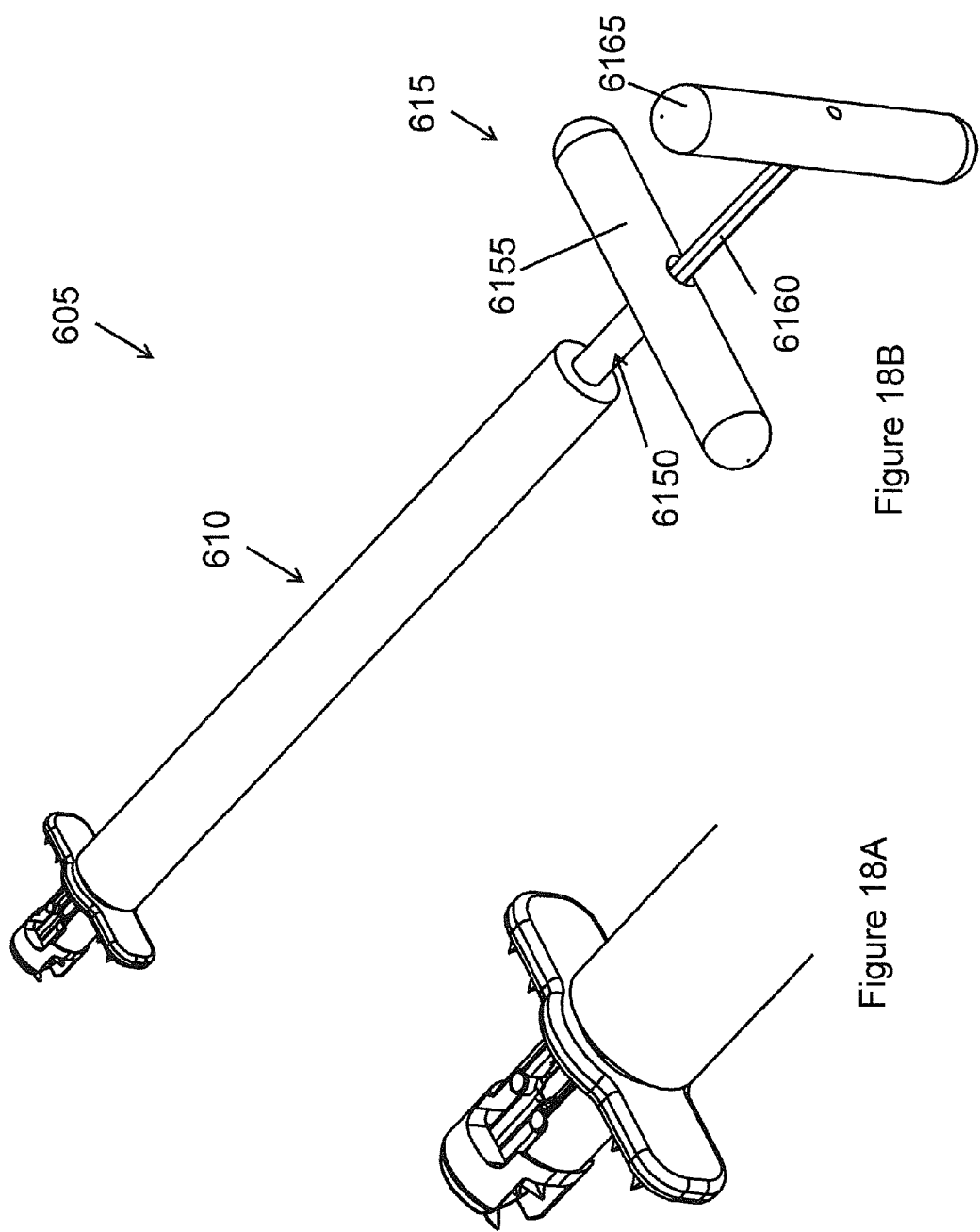

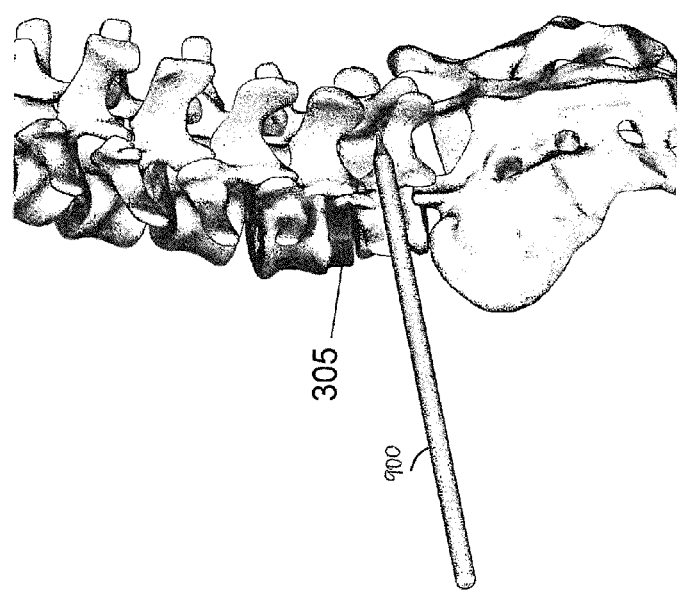
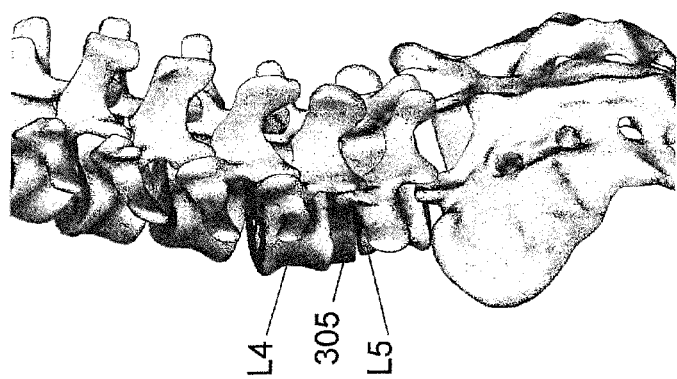

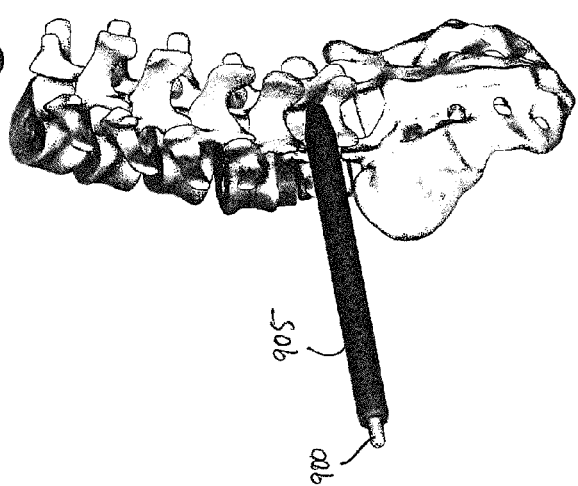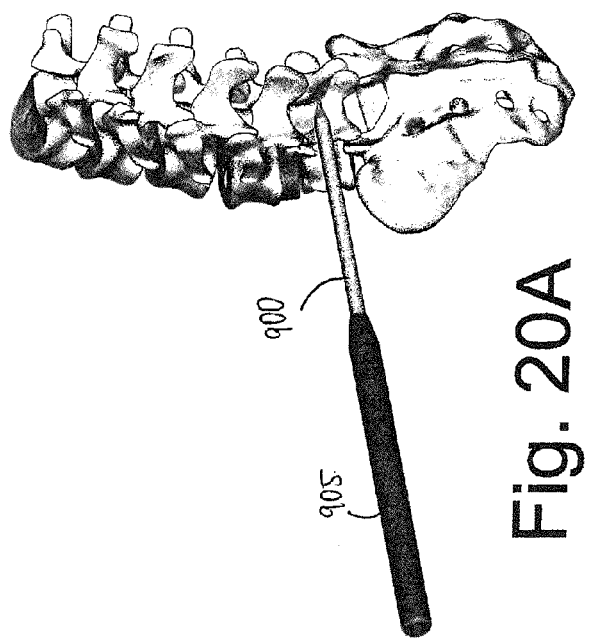

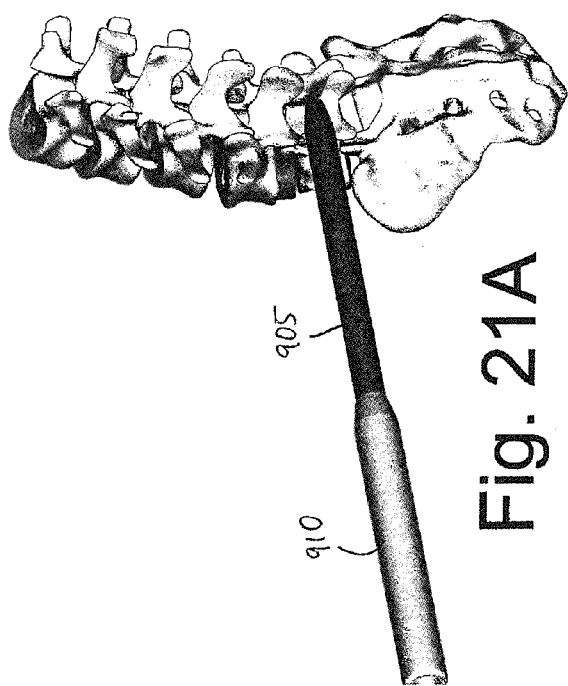
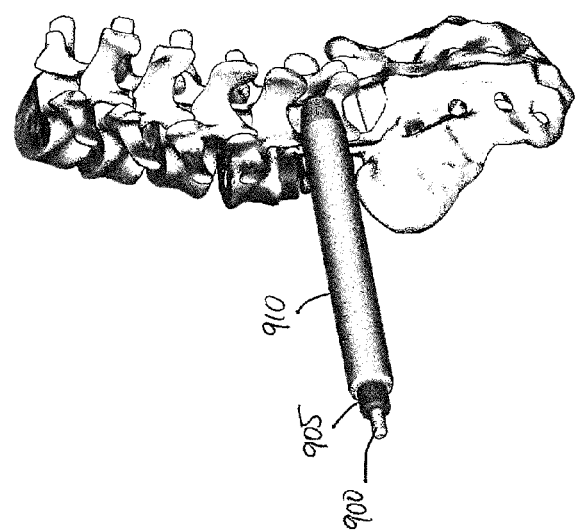

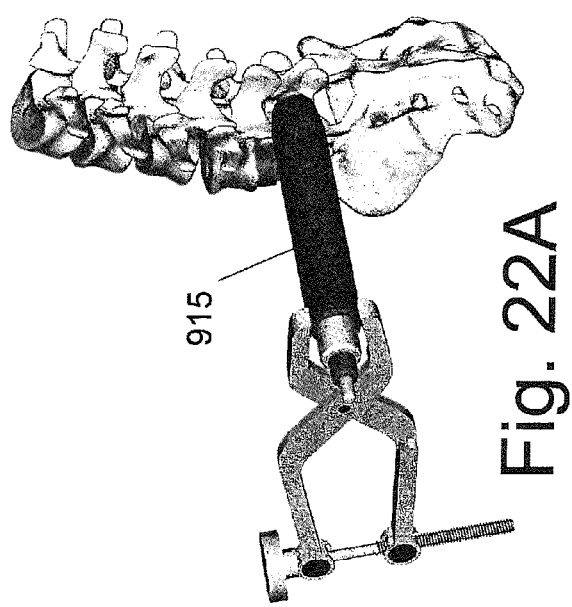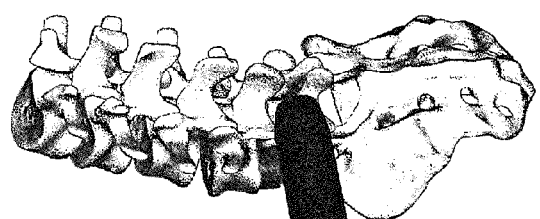

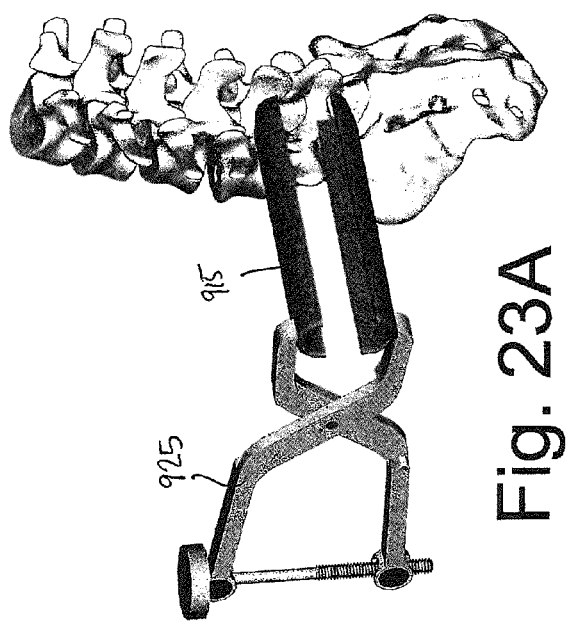
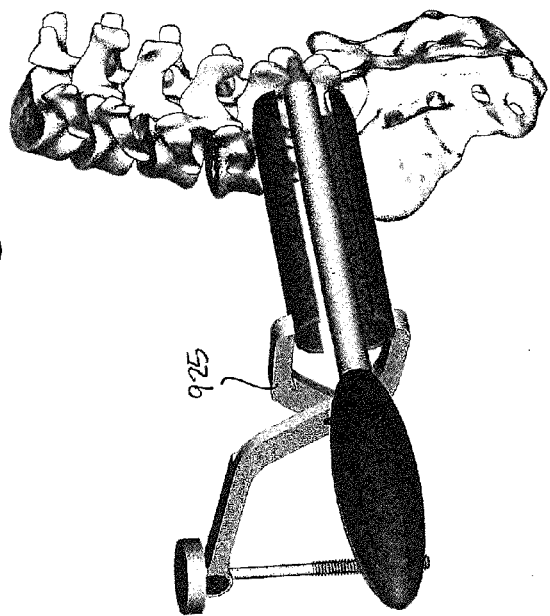

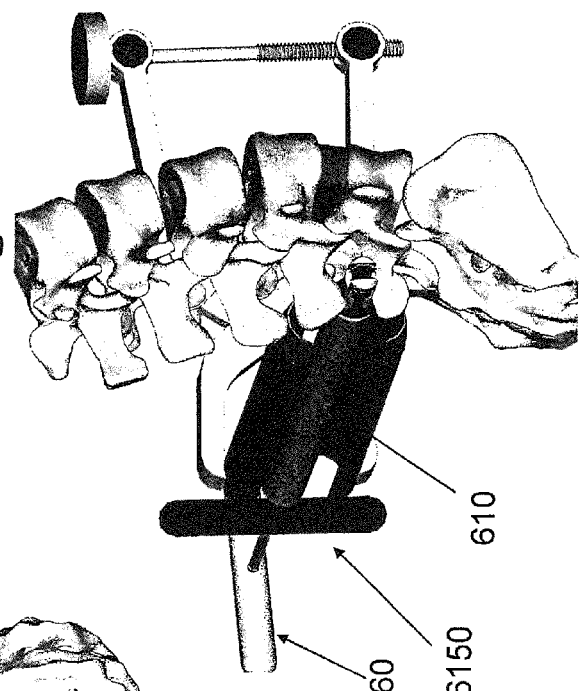
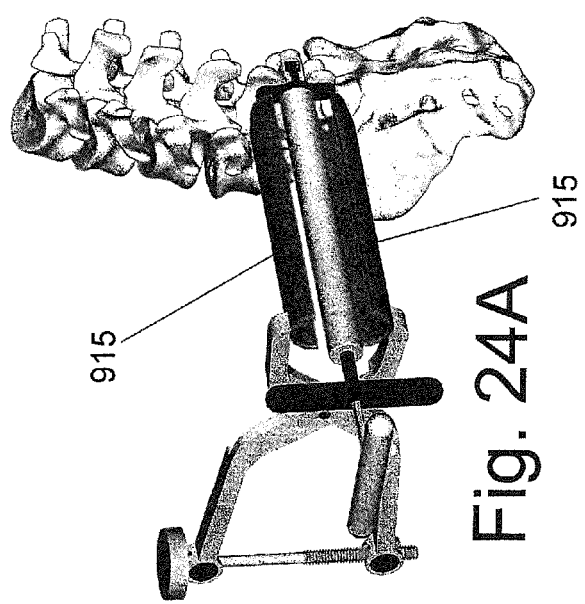

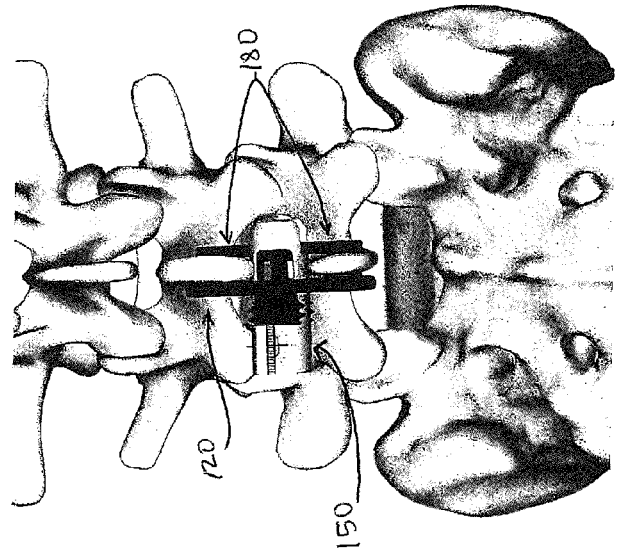
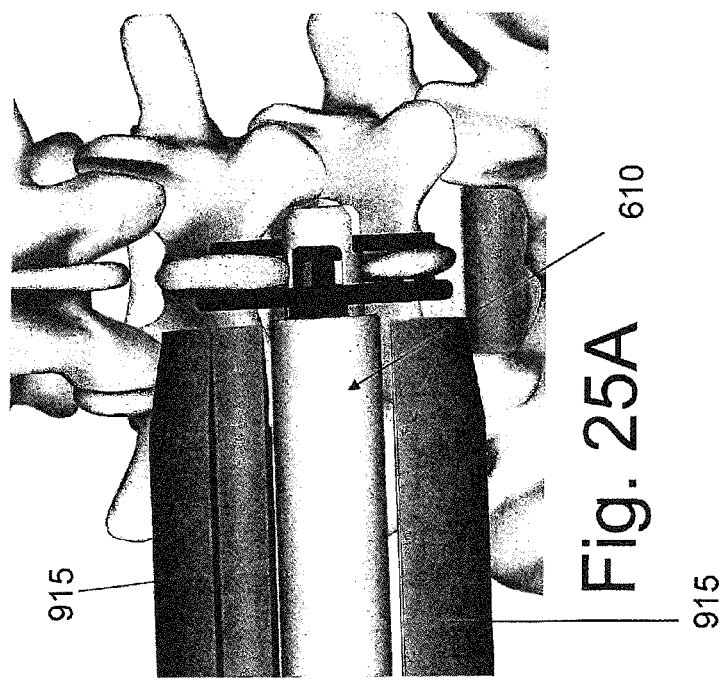

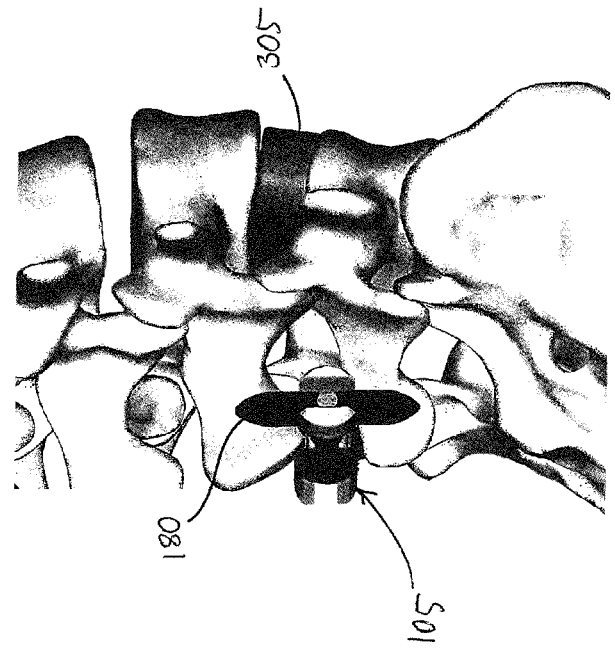
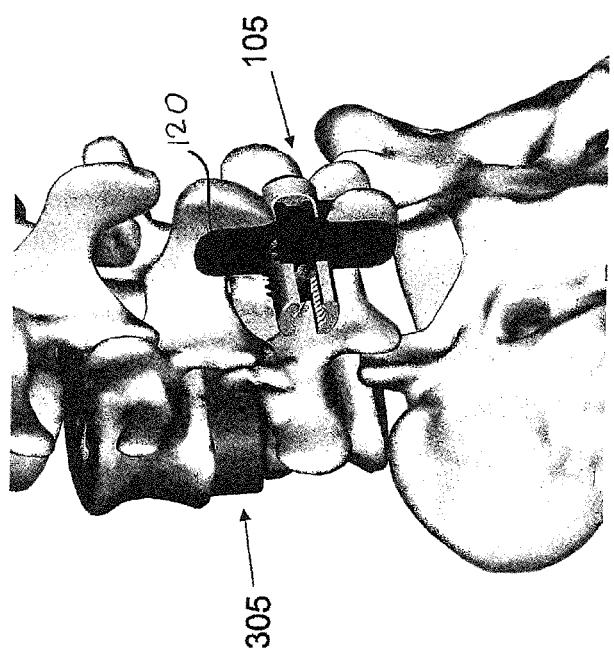

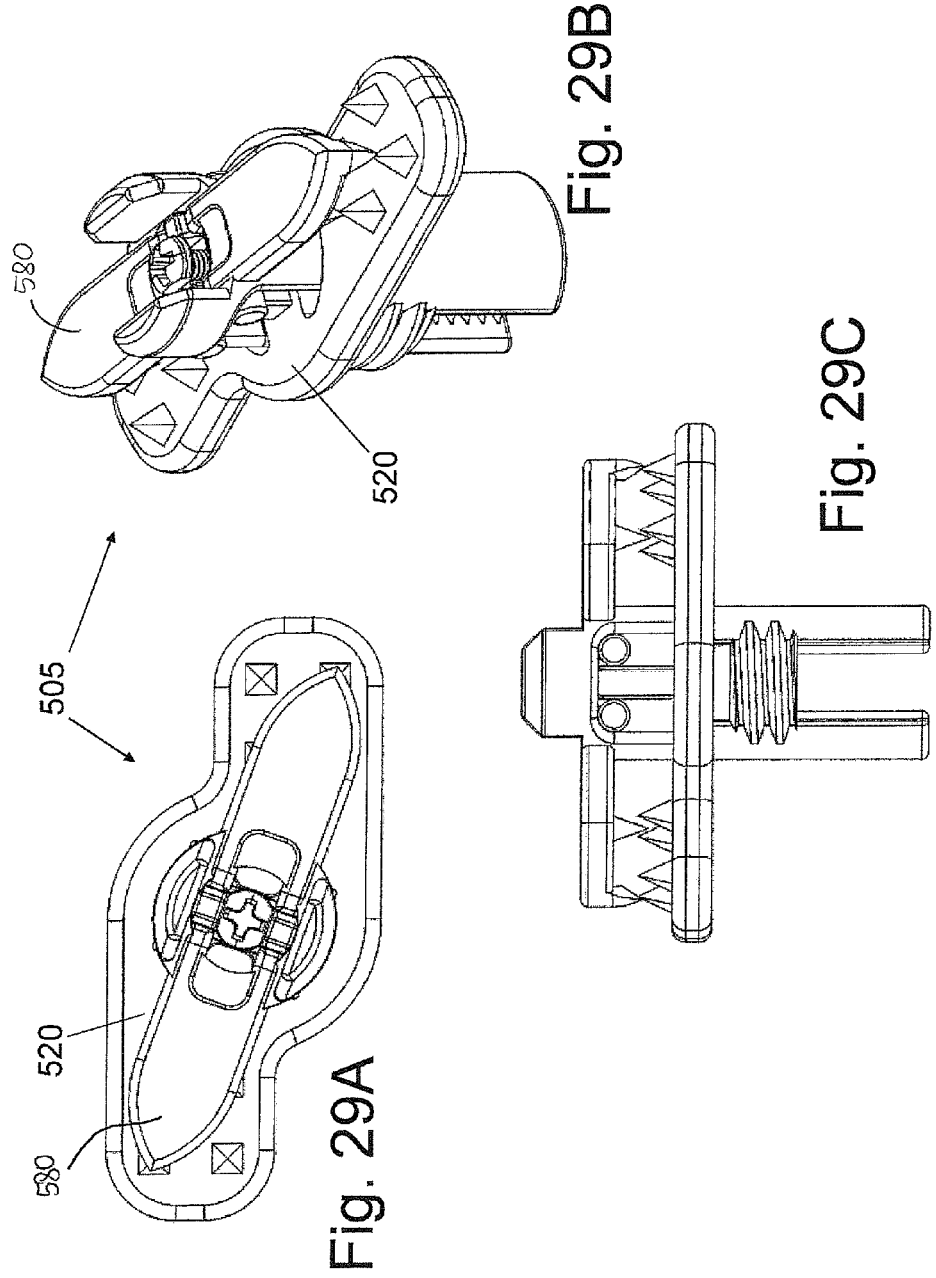

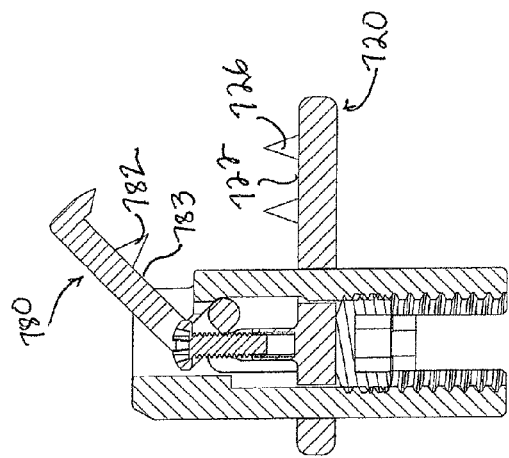
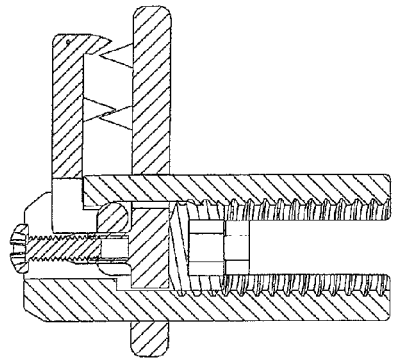
Fig. 31B
Fig. 31C
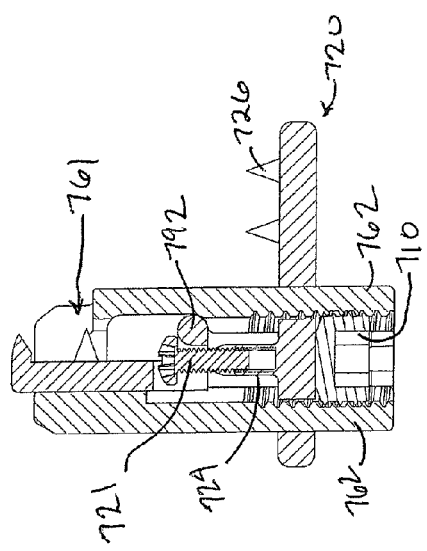
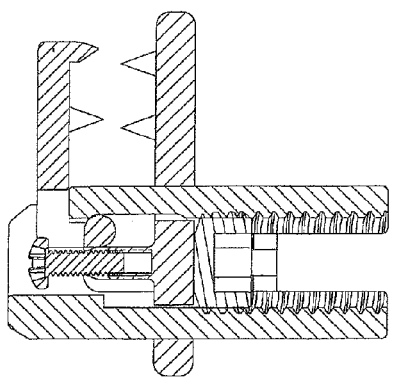
Fig. 31D
Fig. 31E

SPINAL FIXATION DEVICES AND METHODS OF USE

REFERENCE TO PRIORITY DOCUMENT

This application is a continuation of and claims priority to co-owned, co-pending U.S. patent application Ser. No. 12/940,960 filed on Nov. 5, 2010 and issuing as U.S. Pat. No. 8,795,335 on Aug. 5, 2014, which is incorporated herein by reference in its entirety, and which claims priority of U.S. Provisional Patent Application Ser. No. 61/280,666, entitled "Spinal Fixation Devices and Methods of Use" by Samy Abdou and William Taylor, filed Nov. 6, 2009. Priority of the filing date of Nov. 6, 2009 is hereby claimed, and the disclosure of the provisional patent application is hereby incorporated by reference in its entirety.

BACKGROUND

This disclosure relates generally to bone fixation systems, components thereof, and methods of implant placement used to adjust, align and maintain the spatial relationship(s) of adjacent bones or bony fragments after surgical reconstruction of skeletal segments. In particular, this disclosure relates to devices that fixate the spinous processes at one vertebral level with the spinous process of another vertebra.

Whether from degenerative disease, traumatic disruption, infection or neoplastic invasion, alteration in the anatomical relationships between the spinal vertebras can cause significant pain, deformity and disability. Spinal disease is a major health problem in the industrialized world and the surgical treatment of spinal pathology is an evolving discipline. The traditional surgical treatment of abnormal vertebral motion is the complete immobilization and bony fusion of the involved spinal segment and an extensive array of surgical techniques and implantable devices have been formulated to accomplish the treatment objective.

Regardless of the specific objectives of surgery, many surgeons employ implantable devices that maintain the desired spatial relationship(s) between adjacent vertebral bodies. The effectiveness of theses devices is critically dependant on adequate fixation into the underlying bone. While screw fixation into the pedicle portion of the vertebral body has emerged as a common method of device fixation, it remains a substantial operation with multiple shortcomings.

SUMMARY

There remains a need for improved devices for adequately fixing and decompressing adjacent bones in the spinal canal in a minimally invasive manner that can be implanted without excessive manipulation and repositioning of the patient during the procedure.

In a first aspect, disclosed is an orthopedic implant for fixing adjacent bones. The implant includes an elongated body extending along a central axis from a first segment to a second segment, and a first rigid abutment surface positioned at the first segment of the elongated body. The first rigid abutment surface is adapted to abut a first bony surface of a bone segment, and the first rigid abutment surface has a long axis. The implant also includes a second rigid abutment surface positioned at the second segment of the elongated body. The second rigid abutment surface is adapted to abut a second bony surface of the bone segment. The implant also includes a locking mechanism that is at least partially positioned at the second segment of the elongated body and adapted to be advanced by a locking instrument. Advancement of the locking mechanism in a first direction produces rotation of the first rigid abutment surface from a first orientation to a second orientation. The long axis of the first rigid abutment surface is substantially parallel to the central axis of the elongated body when in the first orientation and the long axis of the first rigid abutment surface is substantially perpendicular to the central axis of the elongated body when in the second orientation. Continued advancement of the locking mechanism produces advancement of the first rigid abutment surface towards the second rigid abutment surface and placement of a compressive load onto the first bony surface and the second bony surface. The compressive load is sufficient to immobilize the implant relative to the first bony surface and the second bony surface.

At least the first rigid abutment surface can have at least one sharpened protrusion that is adapted to penetrate and anchor onto the first bony surface. The compressive load can forcibly advance the at least one sharpened protrusion into the first bony surface. The second rigid abutment surface can have at least one sharpened protrusion that is adapted to penetrate and anchor onto the second bony surface. The compressive load can forcibly advance the at least one sharpened protrusion into the second bony surface. The locking mechanism can be further adapted to retain the compressive load placed onto the first bony surface and the second bony surface after disengagement of the locking instrument from the locking mechanism. Rotation of the first rigid abutment surface from the first orientation to the second orientation can be reversed by advancement of the locking mechanism in a second direction that is opposite to the first direction.

In another aspect, disclosed is a method for the percutaneous decompression of the spinal canal. The method includes identifying on X-ray a spinal level to be decompressed; making an incision that is lateral to the vertebral midline; and advancing an orthopedic implant into an interspinous space of the spinal level to be decompressed. The implant includes an elongated body extending along a central axis from a first segment to a second segment, and a first rigid abutment surface positioned at the first segment of the elongated body. The first rigid abutment surface is adapted to abut a first bony surface of a bone segment, and the first rigid abutment surface has a long axis. The implant also includes a second rigid abutment surface positioned at the second segment of the elongated body. The second rigid abutment surface is adapted to abut a second bony surface of the bone segment. The implant also includes a locking mechanism that is at least partially positioned at the second segment of the elongated body and adapted to be advanced by a locking instrument. Advancement of the locking mechanism in a first direction produces rotation of the first rigid abutment surface from a first orientation to a second orientation. The long axis of the first rigid abutment surface is substantially parallel to the central axis of the elongated body when in the first orientation and the long axis of the first rigid abutment surface is substantially perpendicular to the central axis of the elongated body when in the second orientation. Continued advancement of the locking mechanism produces advancement of the first rigid abutment surface towards the second rigid abutment surface and placement of a compressive load onto the first bony surface and the second bony surface. The compressive load is sufficient to immobilize the implant relative to the first bony surface and the second bony surface.

In another aspect, disclosed is a method for the anterior and posterior decompression of the spinal canal between a first superior vertebral bone and a second inferior vertebral bone. The method includes identifying on X-ray a spinal level to be decompressed; placing a first orthopedic implant into the anterior column of the spinal level to be decompressed. The first implant is positioned within the disc space between the first superior vertebral bone and the second inferior vertebral bone. The method also includes advancing a second orthopedic implant into an interspinous space between the spinous processes of the first superior vertebral bone and the second inferior vertebral bone. The second implant is advanced into the interspinous space in a percutaneous manner. The second implant is adapted to rigidly immobilize the spinous processes of the first superior vertebral bone and the second inferior vertebral bone relative to one another. The second implant includes an elongated body extending along a central axis from a first segment to a second segment, and a first rigid abutment surface positioned at the first segment of the elongated body. The first rigid abutment surface is adapted to abut a first bony surface of a bone segment, and the first rigid abutment surface has a long axis. The second implant also includes a second rigid abutment surface positioned at the second segment of the elongated body. The second rigid abutment surface is adapted to abut a second bony surface of a bone segment. The second implant also includes a locking mechanism that is adapted to be engaged by a locking instrument. Advancement of the locking mechanism in a first direction produces advancement of the first rigid abutment surface towards the second rigid abutment surface and placement of a compressive load onto the first bony surface and the second bony surface. The applied compressive load is sufficient to immobilize the second implant relative to the spinous processes of the first and second vertebral bones.

In another aspect, disclosed is a device for the treatment of abnormal spinal stability and stenosis of the spinal canal. The device includes a plate member having a first abutment surface and an opening extending through a portion of the plate member; a deployment element having a cross-sectional shape complementary to the opening of the plate member and an inner threaded surface; a locking mechanism that engages the inner threaded surface of the deployment member to produce downward translation of the deployment member through the opening of the plate member; and a rotation arm moveably coupled to the deployment element and having a second abutment surface extending outward from a central hinge element.

In yet another aspect, a method for fusion of a spinal segment comprising a superior vertebral bone, an immediately adjacent inferior vertebral bone and an intervening intervertebral disc space of a subject is disclosed. In one embodiment, the method comprises: (i) identifying the spinal segment on an imaging modality; (ii) advancing a first implant into the intervertebral disc using a first corridor within the subject that extends from a first lateral skin incision, through a psoas muscle and onto a lateral side surface of the intervertebral disc space; (iii) positioning the first implant within the intervertebral disc space through the first corridor; (iv) advancing a second implant through a second corridor and onto a lateral aspect of an interspinous space, the interspinous space being positioned between a spinous process of the superior vertebral bone and a spinous process of the inferior vertebral bone, the second implant comprising: an elongated body configured to extend along a longitudinal axis from a proximal segment to a distal segment; a first bone abutment member configured to extend along a longitudinal axis from a proximal to a distal end and movably coupled to the distal segment of the elongated body; and a second bone abutment member configured to extend along a longitudinal axis from a proximal to a distal end and coupled to the proximal segment of the elongated body; (v) positioning the elongated body of the second implant at least partially within the interspinous space, the first bone abutment member being positioned on a side of the interspinous space contralateral to the first lateral skin incision, and the second bone abutment member being positioned on a side of the interspinous space ipsilateral to the first lateral skin incision; (vi) actuating a locking mechanism of the second implant, the act of actuating advancing the first and the second bone abutment members towards one another; and (vii) immobilizing the spinous process of the superior vertebral bone relative to the spinous process of the inferior vertebral bone.

In another aspect, a method for stabilizing a spinal segment comprising a superior vertebral bone, an immediately adjacent inferior vertebral bone and an intervening intervertebral disc space is disclosed. In one embodiment, the method comprises: (i) identifying the spinal segment using an imaging modality; (ii) creating a first corridor configured to extend through a psoas muscle and onto a lateral side surface of the intervertebral disc space; (iii) advancing a first implant at least partially into the intervertebral disc space using the first corridor; (iv) advancing a second implant through a second corridor configured to extend onto a lateral aspect of an interspinous space positioned between a spinous process of the superior vertebral bone and a spinous process of the inferior vertebral bone, the second corridor being ipsilateral to the first corridor, and the second implant comprising: an elongated body configured to extend along a longitudinal axis from a proximal segment to a distal segment; a first bone abutment member configured to extend along a longitudinal axis from a proximal to a distal end and movably coupled to the distal segment of the elongated body; and a second bone abutment member configured to extend along a longitudinal axis from a proximal to a distal end and coupled to the proximal segment of the elongated body; (v) advancing the second implant at least partially into the interspinous space, the first and the second bone abutment members of the second implant being positioned on opposing sides of at least one of the spinous process of the superior vertebral bone and/or the spinous process of the inferior vertebral bone; (vi) performing a first actuation of a locking mechanism of the second implant, the first actuation thereof causing rotation of the longitudinal axis of the first bone abutment member to a greater angle with respect to the longitudinal axis of the elongated body; (vii) performing a second actuation of the locking mechanism of the second implant, the second actuation thereof causing translation of the bone abutment members toward one another without further rotation of the first bone abutment member relative to the elongated body; and (viii) immobilizing the spinous process of the superior vertebral bone relative to the spinous process of the inferior vertebral bone.

In a further aspect, a method for bony fusion of a first vertebral bone, an immediately adjacent second vertebral bone, and an intervening intervertebral disc space is disclosed. In one embodiment, the method comprises: (i) identifying the first and second vertebral bones on an imaging modality; (ii) placing a skin incision posterior to a posterior aspect of a pedicle of an inferior one of the first and second vertebral bones; (iii) developing a first corridor to an ipsilateral facet joint from the incision, the facet joint comprising an articulation between the first and second vertebral bones; (iv) removing at least a portion of the facet joint; (v) advancing at least a segment of a first implant into the intervertebral disc space through a trans-foraminal corridor; (vi) developing a second corridor to the lateral aspect of an inter-spinous space, the inter-spinous space being positioned between a spinous process of the first vertebral bone and a spinous process of the second vertebral bone; (vii) positioning a second implant within the interspinous space, the second implant comprising: an elongated body configured to extend along a longitudinal axis from a proximal segment to a distal segment; a first bone abutment member configured to extend along a longitudinal axis from a proximal to a distal end and movably coupled to the distal segment of the elongated body; and a second bone abutment member configured to extend along a longitudinal axis from a proximal to a distal end and coupled to the proximal segment of the elongated body; (viii) positioning the elongated body of the second implant at least partially within the interspinous space, the first bone abutment member being positioned on a side of the interspinous space contralateral to the skin incision, and the second bone abutment member being positioned on a side of the interspinous space ipsilateral to the skin incision; (ix) actuating a locking mechanism of the second implant to advance the first and the second bone abutment members towards one another; and (x) immobilizing the spinous process of the first vertebral bone relative to the spinous process of the second vertebral bone.

In yet another aspect, a method for anterior and posterior decompression of a target spinal canal segment that is positioned between a superior vertebral bone and an inferior vertebral bone is disclosed. In one embodiment the method comprises: (i) identifying the target segment; (ii) placing a first implant within a disc space that is positioned between the superior vertebral bone and the inferior vertebral using a first corridor configured to extend from a posterior skin incision and through at least a portion of a facet joint that forms an articulation between the superior and inferior vertebral bones; (iii) advancing a second implant into an interspinous space between a spinous process of each of the superior and inferior vertebral bones, the second implant comprising: an elongated body configured to extend along a longitudinal axis from a proximal segment to a distal segment; a first bone abutment member configured to extend along a longitudinal axis from a proximal to a distal end and movably coupled to the distal segment of the elongated body; and a second bone abutment member configured to extend along a longitudinal axis from a proximal to a distal end and coupled to the proximal segment of the elongated body; (iv) positioning the first and second bone abutment members of the second implant on opposing sides of at least one of the spinous processes of the superior and inferior vertebral bones; (v) performing a first actuation of a locking mechanism of the second implant, the first actuation thereof causing rotation of the longitudinal axis of the first bone abutment member to a greater angle with respect to the longitudinal axis of the elongated body; (vi) performing a subsequent actuation of the locking mechanism of the second implant, the subsequent actuation thereof causing translation of the bone abutment members toward one another without further rotation of the first bone abutment member relative to the elongated body; and (vii) immobilizing the spinous process of the superior vertebral bone relative to the spinous process of the inferior vertebral bone.

The details of one or more embodiments are set forth in the accompanying drawings and description below. Other features, objects, and advantages will be apparent from the following description, the accompanying drawings and from the claims.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

FIG. 2 is an exploded view of the device of FIG. 1;

FIGS. 4A-4B are various views of a functional spinal unit including two adjacent vertebral bones;

FIG. 5 is a cross-sectional view of a torso at the level of the lumbar spine;

FIGS. 7A-7B are perspective views of a plate member according to one embodiment;

FIGS. 8A-8B are perspective views of an advancing deployment member according to one embodiment;

FIGS. 9A-9B are perspective views of a rotation arm according to one embodiment;

FIGS. 10A-10C are various views of a locking nut;

FIGS. 11A-11B are cross-sectional views of the fixation device of FIG. 1 in a fully withdrawn state of the delivery configuration;

FIGS. 12A-12B are cross-sectional views of the fixation device of FIG. 1 in a partially deployed state;

FIGS. 13A-13B are cross-sectional views of the fixation device of FIG. 1 in a deployed state;

FIGS. 14A-14B are side views of the fixation device in the withdrawn state;

FIGS. 15A-15B are side views of the fixation device in the deployment state;

FIG. 16A-16B is a side view of the fixation device in the fully deployed state and the downward translation of fully rotated arms towards plate member;

FIGS. 17A-17B are perspective views of a fixation device in the withdrawn state coupled to a deployment device;

FIGS. 18A-18B are perspective views of the deployment device of FIGS. 17A-17B;

FIG. 19A shows a spine with an implant positioned within a disc space between adjacent vertebrae;

FIG. 19B shows a tissue dilator positioned through a lateral corridor to the spinous processes of the adjacent vertebrae;

FIGS. 20A-20B show placement of a larger tissue dilator over the tissue dilator of FIG. 19B;

FIGS. 21A-21B show placement of a larger tissue dilator over the tissue dilators of FIGS. 20A-20B and FIG. 19B;

FIGS. 22A-22B show placement of a distraction device advanced into the interspinous space created by the tissue dilators;

FIGS. 23A-23B show distraction using the distraction device of FIGS. 22A-22B and dilation of the space between the spinous processes upon ligament perforation;

FIGS. 24A-24B show guidance to the interspinous space the fixation device coupled to the deployment device and advancement into the space between the spinous processes;

FIGS. 25A-25B show deployment of the fixation device from the withdrawn state to the deployed state to capture the spinous processes and immobilize them relative to one another;

FIGS. 26A-26B show the fixation device deployed and the deployment instrument and distraction device removed;

FIGS. 29A-29C illustrate another embodiment of a fixation device having a plate with a "z" configuration;

FIGS. 31A-31 E illustrate another embodiment of a fixation device;

Figure 1:
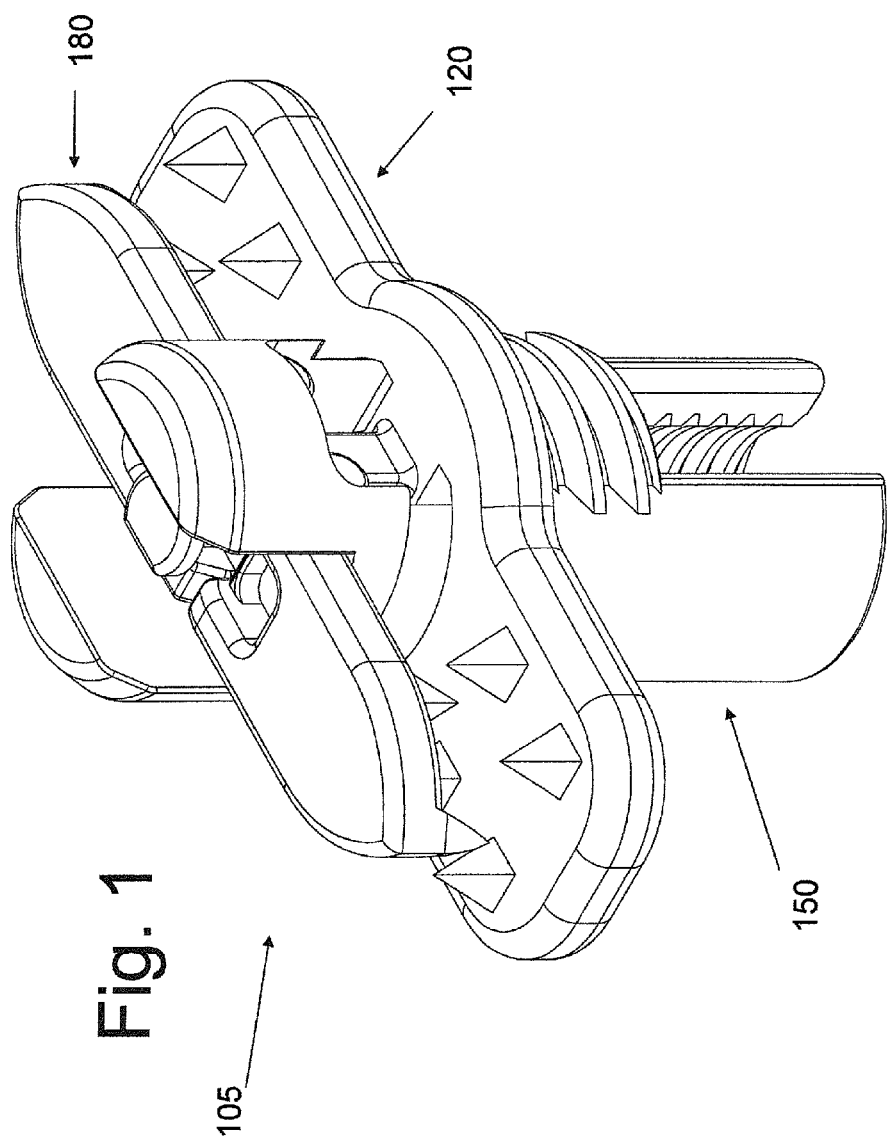
FIG. 1 is a perspective view of a first embodiment of a fixation device.

In order to promote an understanding of the principals of the disclosure, reference is made to the drawings and the embodiments illustrated therein. Nevertheless, it will be understood that the drawings are illustrative and no limitation of the scope of the claims is thereby intended. Any such alterations and further modifications in the illustrated embodiments, and any such further applications of the principles of the disclosed devices as illustrated herein are contemplated as would normally occur to one of ordinary skill in the art.

DETAILED DESCRIPTION

Described herein are devices, systems and methods for the treatment of abnormal spinal stability and stenosis of the spinal canal by the implantation of orthopedic devices between skeletal segments. The implanted devices can be used to adjust, decompress and maintain the spatial relationship(s) of adjacent bones. Depending on the implant design, the motion between the skeletal segments may be returned to normal, increased, modified, limited or completely immobilized.

In a first embodiment, a device is disclosed that rigidly fixates the spinous processes of two adjacent vertebral bones relative to one another. In a preferred embodiment of device use, the implant is percutaneously placed into the interspinous space and used to provide decompression of spinal stenosis by retaining the spinous process in the distracted position. The implant also rigidly affixes the spinous processes of the vertebral bones on either side of the implanted inter-spinous space in order to retain and immobilize the vertebral bones relative to one another.

The device is preferably inserted from a first side of the interspinous space. Rotatable members of the implant can be advanced across the interspinous space from the first ipsilateral side to the second contralateral side, wherein the long axis of the deployable members can be substantially parallel to the trajectory of device implantation. A locking mechanism can be engaged in order to produce movement of the rotatable members, wherein, in an embodiment, the rotatable members are rotated so that the long axis is substantially perpendicular to the trajectory of device implantation. With further engagement of the locking mechanism, the rotatable members can be translated towards the spinous process and towards an a second implant abutment surface that is located on the side of the spinous processes that is opposite to that of the rotatable members.

As the locking mechanism is advanced further, the spinous processes are forcibly captured between the rotatable members and the second implant abutment surface. In a preferred embedment, the surfaces that abut the spinous process have spiked protrusions that penetrate the bony surface of the spinous processes and rigidly anchor into them. In a preferred embodiment, actuation of the locking mechanism produces rotation of the rotatable arms, translation of the rotatable arms, the forcible capture of the spinous processes (with spike penetration of the bony surface of the spinous processes) between the rotatable members and second abutment surface, and locking the device in that configuration. The locking mechanism is described as a single mechanism that produces the aforementioned functions, however, it is further contemplated that the locking mechanism may consist of at least two mechanisms that collectively perform the aforementioned functions. The locking mechanism is preferably engaged and actuated through a deployment instrument that is substantially positioned parallel to the trajectory of device implantation. Further, the engagble segment of the locking mechanism is preferably located on the ipsilateral side of the spinous processes at the time of engagement by the deployment instrument (whereas the rotatable members are located on the contralateral side of the spinous processes).

In an additional embodiment of implant use, the implant is advanced into the posterior column (into the interspinous space) of a spinal segment while another orthopedic implant is placed into the anterior column of the same spinal segment using a lateral approach to the anterior column. These operations are collectively known in the art as XLIF, DLiF and the like. In this method both implants may be placed through a single lateral skin incision or two immediately adjacent skin incisions to provide a percutaneous or minimally invasive approach. Further, this method provides circumferential (i.e., anterior and posterior) expansion and decompression of the spinal so as to treat spinal stenosis though anterior and posterior decompression of the spinal canal.

In another embodiment of use, the device may be deployed through a single incision that is posterior and lateral to the transverse processes of the spinal level to be implant. This surgical corridor and approach is known to those of ordinary skill in the art as TLiF. Bone screws can be advanced into the pedicle portion of bone on the side of the vertebrae that is ipsilateral to the incision. The screws are rigidly interconnected with a rod. The device disclosed herein is then placed through the same skin incision into the inter-spinous space. While contralateral pedicle screws may be also placed by the operating surgeon, the current inter-spinous device obviates the need for contra-lateral screw placement.

In another device embodiment of the implant, the device rigidly affixes to the spinous process of one but not both adjacent vertebral bones in order to attach the implant to just one vertebral bone. In a method of use of this device embodiment, the implant limits the extent of vertebral extension but permits continued vertebral flexion. Comparable methods of use to those already described are also contemplated.

Bone Fixation Device

FIG. 1 is a perspective view of an embodiment of a fixation device 105 in an assembled and deployed state. FIG. 2 shows a perspective view of the device 105 in an exploded view. The fixation device 105 includes a plate member 120, rotation arm 180, and an advancing deployment member 150, each of which will be described in more detail below. The fixation device 105 can also include a locking nut 210 and a screw 220 (shown in FIG. 2), which each play a role in translation, fixation and compression of the device 105 into the deployed state. The device 105 can be used to interconnect, fixate and compress the spinous process at one vertebral level with the spinous process of another adjacent vertebral level. In use, actuation of locking nut 210 produces rotation and translation of rotation arms 180, thereby sandwiching and rigidly affixing the spinous process against plate member 120, as will be described in more detail below. The disclosed devices permit a surgeon to implant the device into the posterior column of the spine from a lateral, or flank incision, as will be discussed in more detail below.

As used herein, the anterior column generally designates a portion of the vertebral body and/or Functional Spinal Unit (FSU) that is situated anterior to the posterior longitudinal ligament. Thus, its use in this application encompasses both the anterior and middle column of Denis (see "The three column spine and its significance in the classification of acute thoracolumbar spinal injuries." Denis, F. *Spine* 1983 November-December; 8(8):817-31, which is incorporated by reference in its entirety.) The illustrations and definitions of anatomical structures are known to those of ordinary skill in the art. They are described in more detail in *Atlas of Human Anatomy*, by Frank Netter, third edition, Icon Learning Systems, Teterboro, N.J. The text is hereby incorporated by reference in its entirety. It should be appreciated that the directional language and terms regarding orientation such as upper, lower, upward, downward etc. are used throughout merely for convenience of description and are not intended to be limiting.

Figure 3A:
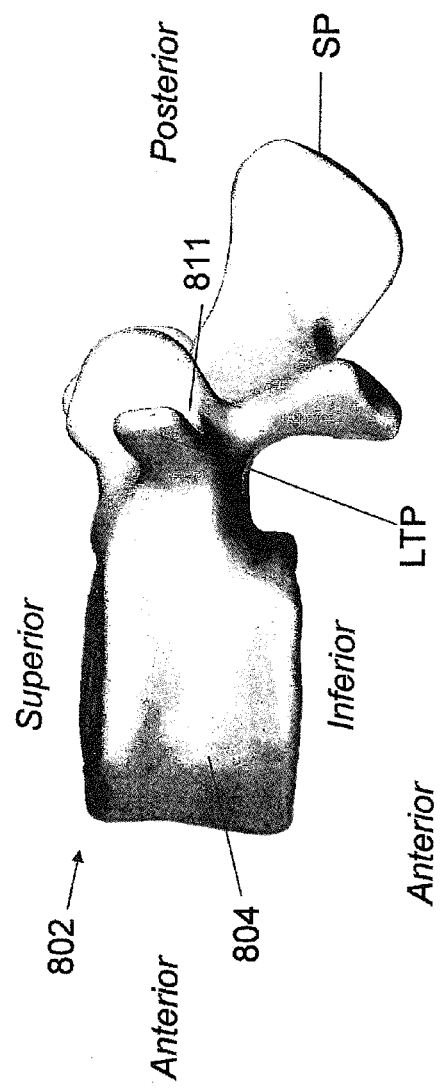
FIGS. 3A-3C are various views of a diagrammatic representation of a spinal vertebral bone.
Figure 3B:
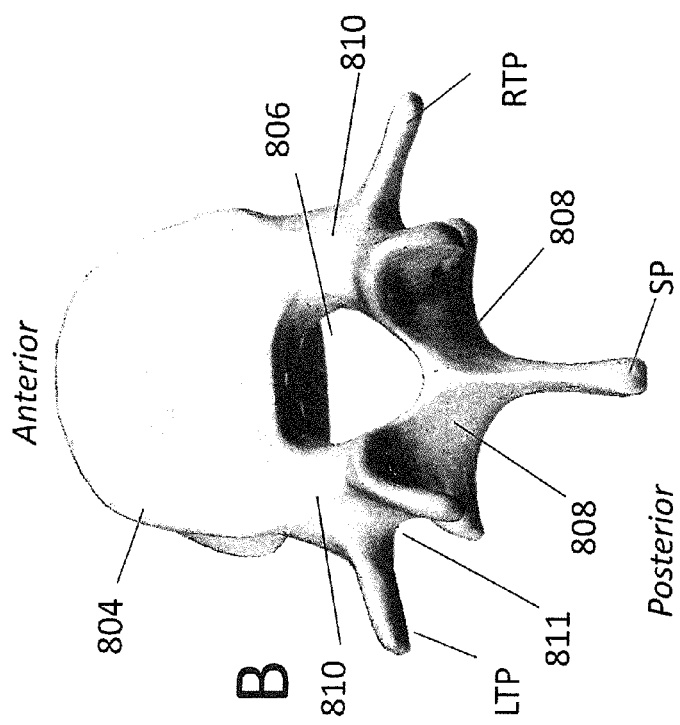
Figure 3C:
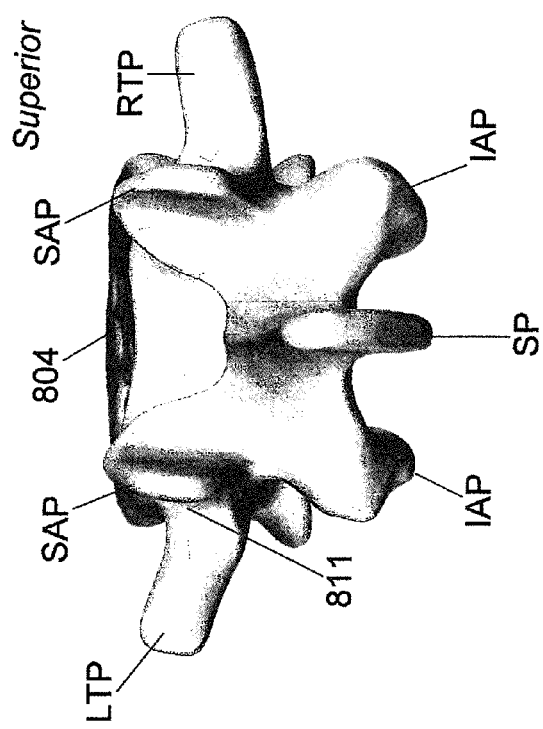

FIGS. 3A-3C show diagrammatic representations of a spinal vertebral bone 802 in multiple views. For clarity of illustration, the vertebral bone of FIGS. 3A-3C and those of other illustrations disclosed herein are represented schematically and it should be appreciated that actual vertebral bodies may include anatomical details that are not shown in these figures. Further, it is understood that the vertebral bones at a given level of the spinal column of a human or animal subject will contain anatomical features that may not be present at other levels of the same spinal column. The illustrated vertebral bones are intended to generically represent vertebral bones at any spinal level without limitation. The disclosed devices and methods may be applied at any applicable spinal level.

Vertebral bone 802 contains an anteriorly-placed vertebral body 804, a centrally placed spinal canal 806 and posteriorly-placed lamina 808. The pedicle segments 810 of vertebral bone 802 form the lateral aspect of the spinal canal 806 and connect the laminas 808 to the vertebral body 804. The spinal canal 806 contains neural structures such as the spinal cord and/or nerves. A midline protrusion termed the spinous process SP extends posteriorly from the medial aspect of laminas 808. A protrusion extends laterally from each side of the posterior aspect of the vertebral bone 802 and is termed the transverse process TP. A right transverse process RTP extends to the right and a left transverse process L TP extends to the left. A superior protrusion extends superiorly above the lamina 808 on each side of the vertebral midline and is termed the superior articulating process SAP. An inferior protrusion extends inferiorly below the lamina 808 on each side of the vertebral midline and is termed the inferior articulating process IAP. Note that the posterior aspect of the pedicle 810 can be accessed at an indentation 811 in the vertebral bone 802 between the lateral aspect of the SAP and the medial aspect of the transverse process TP. In surgery, it can be common practice to anchor a bone fastener into the pedicle portion 810 of a vertebral bone 802 by inserting the fastener through indentation 811 and into the underlying pedicle 810.

FIGS. 4A and 4B illustrate a FSU, which includes two adjacent vertebrae and the intervertebral disc between them. The intervertebral disc resides between the inferior surface of the upper vertebral body and the superior surface of the lower vertebral body, although it is not specifically shown in the figures. FIG. 4A shows the posterior surface of the adjacent vertebrae and the articulations between them. FIG. 4B shows an oblique view. The FSU contains a three joint complex between the two vertebral bones, with the intervertebral disc comprising the anterior joint. The posterior joints include a facet joint 814 on each side of the midline, wherein the facet joint 814 contains the articulation between the IAP of the superior vertebral bone and the SAP of the inferior bone.

The interspinous space is generally defined as the space immediately between the spinous processes of a superior vertebral bone and the spinous process of an immediately adjacent inferior vertebral bone. The interspinous space is limited anteriorly by the spinal canal 806 and posteriorly by the posterior tip of the spinous processes. The right lateral aspect of the interspinous space is limited by the right lateral side of the spinous processes whereas the left lateral aspect of the interspinous space is limited by the left lateral side of the spinous processes. Note that the spinous processes of adjacent vertebral bones may be rotated in the axial plane relative to one another because of biological and/or individual variation (schematically shown in FIG. 4A). The interspinous space would continue to be defined as residing between the spinous processes of the superior and inferior vertebral bones.

Now with respect to FIGS. 7A-7B, the plate member 120 of the fixation device 105 includes a generally flat, elongate platform having a first, bone-engaging surface 122 and an opposite, second surface 123. The first surface 122 of the plate member 120 can have one or more elements 126 positioned on either side of a central protrusion 124. Elements 126 can be sharpened such that they can penetrate, grip and can be driven into bone so as to anchor plate member 120 and compress the vertebral bone. The plate member 120 can have two elongate platform regions on either side of the central protrusion 124 or can have a single platform region extending in a single direction (see FIGS. 31A-31 E). Also, the geometry of the elongate platform regions can vary (see also FIGS. 29A-29C).

The central protrusion 124 of the plate member 120 can include two upward-extending elements 1240 on either side of a depression or notch 1241. Full thickness holes 132 can be positioned on each side of protrusion 124 and can have a shape complementary to and adapted to accept member 150 therethrough, as will be described in more detail below. A central opening 1242 can be positioned within notch 1241 and can have a shape configured to accept screw 220. Unlike holes 132, central opening 1242 need not extend fully through plate member. Plate member 120 can have a coupling element 136 on the second surface 123 opposite the central protrusion 124. The coupling element 136 can include a pair of opposing projections each of which can have a threaded outer surface 1360 and a notched inner surface 1364 (see FIG. 7B). The coupling element 136 can be used to couple the fixation device 105 to a deployment instrument for insertion and implantation, as will be described in more detail below.

While plate 120 is shown having two rigid side arms with surfaces 122 and spiked protrusions 126, it is contemplated that the arms can alternatively be made deployable—as shown for rotation members 180. In this embodiment, the device is positioned at the implantation site with the long axis of the rotation arms of plate 120 positioned parallel to the placement trajectory. The rotation arms are then rotated so that the long axis of the rotation arms is positioned perpendicular to the placement trajectory. In this way, plate 120 is made with deployable arms instead of the rigid arms.

FIGS. 8A-8S show perspective views of an advancing deployment member 150. Member 150 is a generally cylindrical element having a central bore 154 extending from a first region to a second region. The first region of the member 150 through which central bore 154 extends has opposing, downward-extending elements 162. The second region of the member 150 has opposing, upward-extending elements 160. The cross-section of the opposing, downward-extending elements 162 is complementary to holes 132 in the plate member 120 such that the downward-extending elements 162 can be drawn through the holes 132. The downward-extending elements 162 are shown as being generally cylindrical on their outer surface although it should be appreciated that the geometry of these elements 162 (and as such the geometry of the complementary holes 132 in the plate member 120) can vary. The inner surface of elements 162 facing the central bore 154 can have threads 156. Opposing elements 162 create a channel 165 that intersects central bore 154. The channel 165 has an upper, expanded region that forms a window 164 that is formed by upper surface 1644 and shoulders 1646.

Opposing, upward-extending elements 160 are shown as being partially cylindrical on their outer surface although it should be appreciated that the geometry of these elements can vary. Upward-extending elements 160 can have a generally flat geometry on their inner surface 163 facing the bore 154. The elements 160 create a second channel 161 through member 150 that intersects the upper region of bore 154. Channel 161 has a generally U-shaped geometry formed by inner surfaces 163 of opposing elements 160 and surface 158. The channel 161 in the upper region of member 150 is off-set by approximately 90 degrees from channel 165 and window 164. It should be appreciated that the angle of off-set can vary. Opposing, downward-extending elements 162 can be drawn through holes 132 such that the elements 162 can interdigitate with the coupling element 136 at the inferior surface of the plate member 120. The outer threaded surface of the coupling element 136 is available for engagement by the deployment instrument as will be described in more detail below. The inner threads 156 of the elements 162 are also available for engagement by the locking nut 210, as will also be described below.

FIGS. 9A-9B show perspective views of a rotation arm 180. Although FIGS. 9A-9B show a single rotation arm 180, it should be appreciated that the fixation device 105 can include two rotation arms 180 positioned in adjacent relationship to one another. It should also be appreciated that the paired rotation arms 180 can be coupled together to form an integrated, articulating element or they can be separate components as shown in the figures. It should also be appreciated that the device can include a single rotation arm as will be described with respect to the embodiment of FIGS. 31A-31E.

Rotation arms 180 have a generally flat, elongate extension region 185 extending outward from a central, cylindrical hinge element 192. The elongate extension region 185 of the rotation arms 180 are sized and configured to be contained within member 150 between opposing, upward-extending elements 160 inside bore 154. An end region 191 of each hinge element 192 extends at least partially through a portion of window 164. As such, the rotation arms 180 can translate upward and downward through the bore and between upward-extending elements 160. This upward and downward translation through the bore 154 is limited by the end region 191 of each hinge element 192 extending through the window and abutting shoulder 1646 at a lower end of the window 164 and surfaces 1644 at an upper end of the window 164.

Rotation arms 180 can have an upper surface 183 having an indentation 186 positioned near the central hinge element 192. When the rotation arms 180 are positioned within the bore 154 of member 150, they are approximately perpendicular to the plane of the plate member 120. The hinge elements 192 are adjacent to one another and the end region 191 of each hinge element 192 extends at least partially through a portion of window 164. The upper surface 183 of each rotation arm 180 is in contact with one another or at least in close proximity to each other such that the indentations 186 on the upper surface 183 align with one another forming a pocket 187. The pocket 187 is configured to contain the head of screw 220 can reside (see for example FIG. 11A-11 8).

The rotation arms 180 are configured to rotate or articulate around the axis of the hinge member 192 and relative to the plane of the plate member 120. Each extension region 185 can rotate away from one another and insert down through U-shaped channel 161 until the arms 180 approach a generally parallel position relative to the plate member 120. Like the bone-engaging surface of the plate member 120, rotation arms 180 can have a bone-engaging surface 181 that can have one or more elements 182 extending therefrom. Elements 182 can be somewhat sharpened such that they can penetrate the surface of the spinous processes, grip bone and aid in anchoring and compression of the arms 180 onto the vertebral bone.

Locking nut 219 is shown in FIGS. 10A-10C. Locking nut can have threads 211 on an outer surface and an opening 213 available from an under surface. In an embodiment, the opening 213 can be a hex head opening that can be engaged with a driving tool having a hex shape. It should be appreciated that other configurations besides a hex shape are considered herein. In the assembled state of fixation device 105, the nut 210 can threadedly engage the inner threads 156 on opposing, downward-extending elements 162 of member 150. Nut 210 can have a flattened upper surface 212 configured to contact a portion of the plate member 120 positioned between holes 132 and below central protrusion 124. As the nut 210 is rotated it engages and draws downward the elements 162 of member 150. This threading action results in the elements 162 being drawn downward through holes 132 and the upward translation of rotation arms 180 through bore 154.

The fixation devices described herein can act to space apart the spinous processes and prevent their bottoming out against one another. The fixation devices described herein also fixate the spinous processes relative to one another by compressing them between the plate member and the rotation arms. As will be described in more detail below, the same threading rotation motions used to deploy the rotation arms is also employed to urge the rotation arms and the plate member further together and compress the spinous processes therebetween.

The reversible transition of the assembled fixation device 105 from the fully withdrawn to the fully deployed state can be accomplished by rotation of threaded locking nut 210 and the consequent movement of member 150 relative to plate member 120. FIGS. 11A-11 B show cross-sectional views (see also FIG. 14A-14B for a side view) of the assembled fixation device 105 in the fully withdrawn state. Rotation arms 180 are largely contained within member 150 such that the extensions 185 extend into the upper region of member 150 between elements 160 and the hinge 192 is positioned within window 164. Screw 220 extends through hole 1242 in central protrusion 124 such that the flanged region or the head of screw 220 is positioned within the pocket 187. As described the pocket 187 is formed by the alignment of the indentations 186 on the upper surface of rotation arms 180 when in a state flush with one another. At least a portion of the end region 191 of each side of hinge 192 extends through window 164. When the rotation arms 180 are in their downward-most fully withdrawn position, end region 191 of the hinge element 192 abuts shoulders 1646 (see FIG. 14A). As locking nut 210 is rotated, downward-extending elements 162 of member 150 are drawn through holes 132 of plate member 120. The hinge elements 192 are translated upward through bore of member 150 until end region 191 of the hinge elements 192 abuts surface 1644 (see FIG. 14B) as will be described in more detail below.

FIGS. 12A-12B illustrate a cross-sectional view (see also FIGS. 15A-15B for a side view) of a partially deployed state of an assembled fixation device 105. Member 150 is shown having been drawn partially through holes 132. Rotation arms 180 that had previously been in contact with shoulders 1646 are being translated upward through bore 154 and now approach upper surfaces 1644. As member 150 is drawn through holes 132 in plate member 120, surfaces 1240 of protrusion 124 of plate 120 press against surfaces 188 of rotation arms 180 and force the rotation arms 180 upward through bore 154. Hinge element 192 can travel from shoulder 1646 near a lower end of the window 164 toward the surface 1644 at the upper end of window 164. As the hinge element 192 approaches the upper end of window 164, the rotation arms 180 can begin to rotate around the axis of hinge 192 such that arms 180 rotate away from one another (see FIG. 15A). Once the hinge 192 of rotation arms 180 abuts the upper surface 1644 of window 164 and no translation space remains, the rotation arms 180 are urged to rotate around axis of hinge 192 and travel down into U-shaped channel 161 (see FIG. 15B).

FIGS. 13A-13B show cross-sectional views (see also FIGS. 16A-16B for a side view) of a fixation device 105 in the deployed state. Rotation of locking nut 210 has caused the rotation arms 180 to be forcibly rotated towards the parallel position with respect to the plane of the plate member 120. The upward-extending elements 1240 of protrusion 124 abut against corners 188 of each rotation arm 180. The rotation arms 180 continue to rotate until they are in a substantially ninety degree orientation relative to the plane of the plate member 120. Hinge elements 192 of rotation arms 180 at this point have fully migrated towards and now abut the upper surfaces 1644.

Further rotation of locking nut 210 forces the downward translation of the bone-engaging surface 183 of rotation arms 180 towards bone-engaging surface 122 of plate member 120 until the elements 126, 182 penetrate and compress the bone of the spinous processes therebetween. Note that actuation of locking nut 210 produces rotation of rotation arms 180. After arms 180 have rotated into the desired relationship to plate member 120, further advancement of locking nut 210 produces advancement of the rotated arms 180 towards plate member 120 and the forceful capture of the spinous processes therebetween. In the current embodiment, the rotated arms 180 then translate towards the plate member 120 in order to rigidly affix the spinous process. However, it is understood that continued rotation of the rotation arms (or additional combination motion of rational and translational movement) could be used to forcibly affix the spinous processes. FIGS. 16A-168 show an illustration of translational movement of the rotation arms 180 towards plate 120 after rotation of the rotation arms.

The rotation arms 180 can be rotated and then translated towards plate member 120 so as rigidly capture the spinous processes using a singular mechanism. The rotation arms 180 and plate member 120 need not include another mechanism to forcibly compress the spinous processes. Further, no separate deployment instrument or clamp is required for the device to rigidly capture the bone and lock the implant. In the preferred embodiment of the current invention, a singular locking mechanism produces rotation of the arms 180, compression of the spinous processes between arms 180 and plate 120, and retention of the plate in the locked configuration after rigid fixation of the spinous processes.

While transition of the device from an open configuration (shown in FIG. 14A, FIGS. 11A and 8) to a closed configuration (shown in FIG. 1, FIGS. 13A and 8) has been described in detail, the device can reversibly transition from the closed configuration to the open configuration by rotation of locking nut 210 in the opposite direction. With reverse rotation of locking nut 210, surface 160 of member 150 moves away from nut 210. With continued reverse rotation of nut 210, screw 220 is captured in pocket 187 of rotation arms 180. Further reverse rotation of nut 210 produces forceful rotation back of rotation members 180 till the open configuration of the device (FIG. 14A, FIGS. 11A and 8) is finally achieved.

Deployment Instrument

The fixation device described herein can be implanted using a deployment instrument 605 that can be deployed percutaneously or using minimally-invasive techniques (see FIG. 17A-17B). Deployment instrument 605 includes an elongate shaft 610 and an actuation assembly 615 extending through the elongate shaft 610. The elongate shaft 610 can have a distal end with internal threads (not shown) configured to reversibly couple with outer threads 1360 of coupling elements 136 of the plate member 120. The deployment instrument 605 can be rigidly attached to plate member 120 upon threading engagement between shaft 610 and coupling elements 136 (see FIGS. 18A-18B).

The actuation assembly 615 can include an inner engagement member 6150 having a central bore through which an inner driver 6160 extends. Both inner engagement member 6150 and the inner driver 6160 are independently translatable through the shaft 610 and with respect to each other. Inner engagement member 6150 has a distal portion 6154 having protrusions and a proximal handle portion 6155. The protrusions of the distal portion 6154 can snugly fit within notched inner surface 1364 of coupling element 136 of plate member 120. Handle portion 6155 can be externally available outside the elongate shaft 610 and the patient such that it can be used by the operator to translate and rotate the inner engagement member 6150. Coupling between inner engagement member 6150 to plate member 120 couples them together and allows the operator to manipulate the position of the fixation device 105, for example when fixation device 105 is positioned inside the patient. Inner driver 6160 has a distal driver portion 6164 and a proximal handle portion 6165. The distal driver portion 6164 can be a hex-driver configured to engage opening 213 of nut 210. Rotation of inner driver 6160 produces rotation of locking nut 210 to advance the locking nut 210 within the deployment member. Rotation in a first direction produces translation of the rotation arms 180 in a first direction. Continued rotation of the locking nut 210 in the first direction places a compressive load onto the bony surfaces positioned between the rotation arm and the plate member. The compressive load generated by rotation of the locking nut 210 is sufficient to urge the sharpened protrusions into the bony surfaces and immobilize the device 105 relative to the spinous processes of the first and second vertebral bones. The compressive load on the bones is retained even after disengagement of the deployment instrument 605. Rotation of the locking nut 210 in a second, opposite direction reverses the compressive load and produces translation of the rotation arms 180 in the opposite direction such that they rotate back into a position that is perpendicular to the plate member. Handle portion 6165 can be externally available outside the elongate shaft 610 and the patient such that it can be used by the operator to translate and rotate the inner driver 6160.

Methods of Use

The implantation of the fixation devices will now be described. As mentioned above, the devices perform a spacing function as well as the compression and fixation of adjacent spinous processes such that the spinous process portions of the implanted vertebral bones are locked in position relative to one another. These devices can be implanted using a lateral approach and that same lateral approach can be used to deploy and compress the spinous processes of vertebral bones being treated. By positioning the implant into the desired interspinous space and then advancing the locking nut 210, the rotation arms 180 can be urged to rotate, translate and then forcibly capture and fixate the spinous processes that are adjacent to the implanted interspihous space between the rotation arms 180 and plate 120.

It should be appreciated that the fixation devices described herein may be used with any surgical approach to the posterior aspect of the spine and the disclosed fixation devices can be positioned in the spine using any appropriate surgical method and/or surgical corridor. The fixation devices described herein are particularly adapted to be placed through a lateral surgical approach to the spine that starts with a surgical incision in the posterior aspect of the patient's flank (i.e., side aspect of the abdominal cavity). The fixation devices described herein are also particularly adapted for use in stabilizing the posterior aspect of a spinal segment when a second orthopedic implant is implanted into the disc space of that segment using a lateral, or flank, approach to the disc space. It must be noted that while the lateral approach is employed in a preferred method of use, the implantation procedure of the device is not limited to a lateral approach to the interspinous space.

In an embodiment, the fixation devices are implanted into the lumbar spine using a flank incision and a lateral approach. In this method, the spinal level of desired device implantation can be localized under X-ray guidance. Referring back to FIG. 5, a skin incision can be placed in the flank at the approximate cephalad-caudal level of the implantation site on the spine. FIG. 5 illustrates a cross sectional view of the torso at the level of the lumbar spine. For clarity of illustration, the contents are represented schematically and those skilled in the art will appreciate that an actual cross section of the human torso may include anatomical details not shown in FIG. 5.

Figure 6:
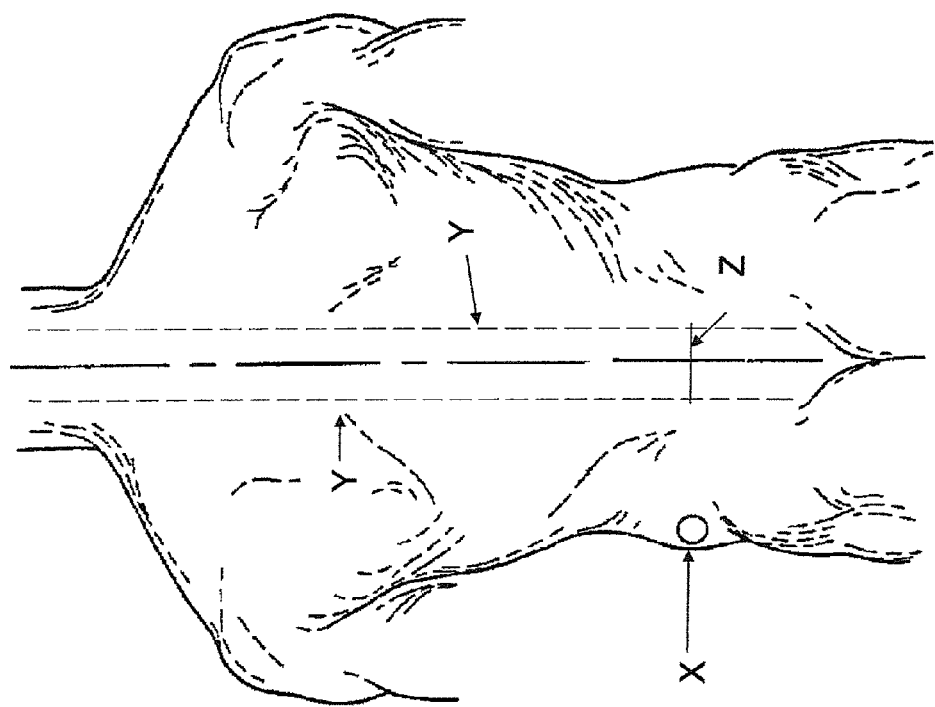
FIG. 6 is a schematic representation of the posterior aspect of a patient.

In preparation for percutaneous placement of the implant into a spinal level, the patient can be, but is not necessarily, placed in a prone or lateral decubitus position. The level of the spine that is to be implanted can be localized on X-ray in at least one plane. After the customary sterile preparation of the operative site, the surgeon can localize an incision point on the skin that is substantially directly lateral to the spinal segment that will be implanted. FIG. 6 shows a schematic representation of the posterior aspect of a patient 117. The skin 118 overlying the back is shown. Lines Y show the lateral extent of the transverse processes of the spinal column. Assuming that the spinal level to be accessed is at line Z, the surgeon can make an incision at or about circle X.

A lateral corridor "Y" (FIG. 5) can be made from the flank, through the psoas muscle 116 and onto the lateral aspect of the disc space at the spinal level to be implanted. An implant can be placed through the corridor Y and into disc space or onto the spine. The procedure is known to those skilled in the art and known as the "XLIF" procedure (see "Extreme Lateral Interbody Fusion (XLIF): a novel surgical technique for anterior lumbar interbody fusion." By Ozgur, Aryan et al. in Spine J. 2006 July-August; 6(4):435-43, which is hereby incorporated by reference in its entirety.)

A second lateral corridor "Z" (FIG. 5) can be made from the flank, through the posterior tissues lateral to the spine and onto the lateral aspect of the spinous processes and inter-spinous ligament of the level to be implanted. While Corridor Y and Corridor Z are shown schematically as exiting the skin 118 of the flank at two different sites, both corridors can be made through a single, common skin incision on the patient's flank. Once through the skin 118, the trajectory can be then varied so as to form an anatomically anterior Corridor Y and an anatomically posterior Corridor Z. The devices disclosed herein can be implanted into the posterior aspect of a functional spinal unit using a Corridor Z and, at the same operation, an implant can be placed into or onto the anterior column (including disc space) of the same functional spinal unit using a Corridor Y.

The method of device implantation is now illustrated. In an embodiment, a functional spinal unit FSU can be targeted for immobilization and fusion. FIG. 19A shows an illustrated spine with implant 305 positioned within the L4/L5 disc space. The level is the functional spinal unit FSU including the L4 and L5 vertebral bones and the intervening disc (not shown). An anterior implant 305 can be placed into the L4/L5 disc space as is known in the art. Implant 305 can be placed into the disc space using a lateral procedure, such as, for example, XLIF, and a lateral surgical corridor such as Corridor Y as described above with respect to FIGS. 5-6. A lateral corridor, such as Corridor Z, can be used to implant fixation device 105. While the anterior implant 305 is illustrated as being implanted first, it is understood that either the anterior or posterior column implant may be positioned first. It should also be understood that a different level of the spine can be targeted for immobilization. For clarity of illustration, the vertebral bones of the illustrations presented herein are represented schematically and those skilled in the art will appreciate that actual vertebral bodies may include anatomical details that are not shown in these figures. It is also understood that the totality of the operation—from selection of the target spinal level to be decompressed, to insertion of the implant to the final placement of implant can be performed under X-ray guidance. Further, the operation can be performed using percutaneous or minimally-invasive surgical techniques with or without the aid of electrophysiological monitoring. The latter include techniques such as electromyography (EMG) and are intended to alert the operating surgeon to the presence of nerves and other neural elements within the surgical corridor. EMG identification of nerves permits the surgeon to navigate the surgical site with increased safety and to lessen the possibility of nerve injury.

FIG. 19B shows a cylindrical tissue dilator 900 placed through a lateral corridor, such as Corridor Z, to the spinous processes of L4 and L5 and the inter-spinous space between them. FIGS. 20A-20B show the placement of a second tissue dilator 905 of greater diameter over the first tissue dilator 900. FIGS. 21A-21B show the placement of a third tissue dilator 910 of still greater diameter over the second tissue dilator 905. FIGS. 22A-22B illustrate the placement of a distraction device having tubular half-receptacles 915 of greater diameter than the third tissue dilator 910. Half-receptacles 915 can be advanced to the L4/L5 inter-spinous space by advancing them atop the third tissue dilator 910. After placement of receptacles 915, the tissue dilators can be removed leaving a central channel 920 to the inter-spinous space (FIG. 22B). The distraction device 925 can be used to distract each half receptacle 915, as shown in FIG. 23A. Note that the distraction device 925 illustrated is generic and that one of ordinary skill in art can provide other distraction devices or even sequential, tissue dilatation with progressively larger tissue dilators that may produce the expanded tissue channel for device implantation. Further, each dilatation step can be checked by intra-operative X-rays at the time of each tissue dilator placement.

EMG may be utilized to identify nerve elements and increase procedure safety. FIG. 23B shows dilatation of the space between the spinous processes (inter-spinous space) and the perforation of the ligament contained therein.

FIG. 24A-24B show the deployment instrument 605 coupled at a distal end to a fixation device 105 in the fully withdrawn state. The deployment instrument 605 and the threadedly attached fixation device 105 are then guided to the interspinous space and the distal end of the fixation device 105 is advanced through the space until at least the channel 161 of member 150 is posterior to the midline of the spinous process. By rotating inner driver 6160, locking nut 210 is rotated and threadedly advanced so that device 105 is transitioned from fully withdrawn (open) state to the fully deployed (closed) state, as previously described. FIG. 25A illustrates the fully deployed fixation device 105 prior to removal of the deployment instrument 605 and receptacles 915.

FIG. 25B and FIGS. 26A-26B show the implanted device 105 with the deployment instrument 605 and receptacles 915 removed. Elements 182 of rotation arms 180 and elements 126 of plate member 120 forcibly penetrate the bone surface and capture each of the L4 and L5 spinous processes. The spinous processes are rigidly immobilized relative to one another by the implanted device 105. As previously mentioned, actuation and advancement of locking nut 210 produces rotation of the rotation arms 180, translation of the rotation arms 180 and the forcible capture of the spinous processes adjacent to the implanted inter-spinous space. In addition, the advanced locking nut 210 serves as a locking mechanism that retains the implant in the deployed configuration. Continued advancement of the locking nut 210 produces advancement of the rotation arms 180 towards the plate member 120 and a placement of compressive loads onto the bony surfaces that they abut and engage. The compressive load is sufficient to immobilize the device relative to the bony surfaces. The sharpened protrusions on the rotation arms 180 and the plate member 120 are forcibly advanced such that they penetrate the bony surfaces. All of these features can be produced though the disclosed mechanism by the singular advancement of a singular locking nut 210.

In the implanted configuration, surface 162 is positioned in the inter-spinous space and abuts the inferior aspect of the superior spinous process and the superior aspect of the inferior spinous process. Surface 162 resists vertebral extension by limiting the extent to which the spinous processes can travel towards one another. Vertebral flexion is also prevented since the captured spinous processes cannot move away from one another. That is, the implant device 105 immobilizes the adjacent spinous processes.

Figure 27A:
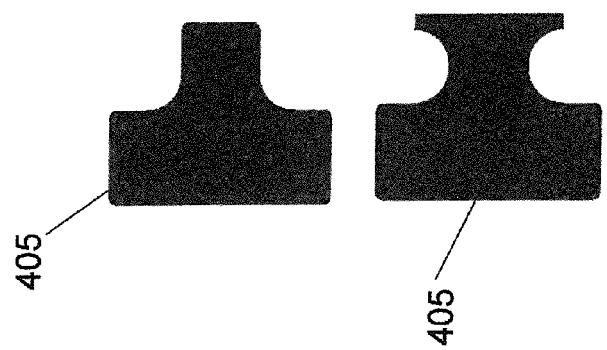
FIG. 27A illustrates embodiments of bone graft material that can be incorporated with the fixation device.
Figure 27B:
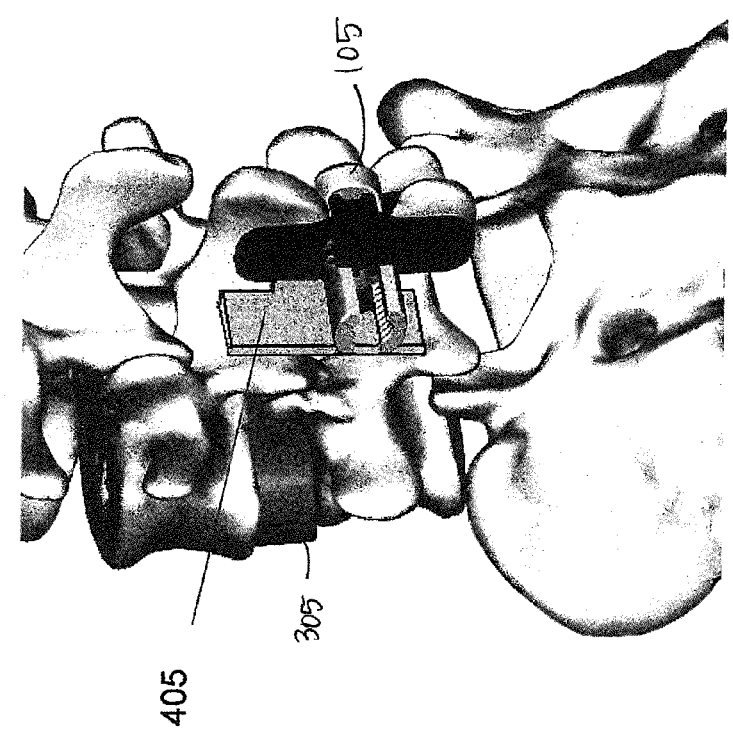
FIG. 27B illustrates bone graft material implanted anterior to the fixation device.
Figure 27D:
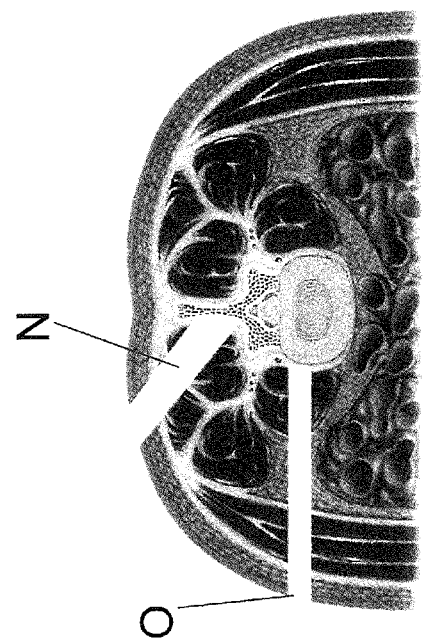
FIGS. 27C and 27D illustrate an alternative method of implant placement.

Bone graft material can be employed in the posterior column to supplement the fixation and bone graft material of the anterior column that is provided by the implant 305. FIG. 27A shows bone graft material 405 (which may include an allograft bone that is machined into the illustrated shapes) having a "T" or "H" shape, but it should be appreciated that other geometries are considered herein. Alternatively, an implant having a hollow central cavity can be used, such as a spacer or a fusion cage (see U.S. Pat. No. 6,375,681, which is hereby incorporated by reference in its entirety) that can be filled with bone graft material. In use, the posterior aspect of the L4 lamina and the posterior aspect of the L5 lamina, as well as the L4 and L5 spinous processes can be denuded of muscle and other soft tissues and the outer bony surface can be de-corticated in preparation for acceptance of a bone graft material. Bone graft material 405 (or a fusion cage) is then placed in apposition with the posterior aspect of the lamina and aspect of the spinous process that is ipsilateral to the side of device insertion. FIG. 27B illustrates use of the graft material 405 positioned anterior to fixation device 105. Note that the bone graft material extends from the lamina and or spinous process of L4 to the lamina and/or spinous process of L5, wherein the bone graft material is adapted to form a fusion mass between the posterior bony elements of L4 and the posterior bony elements of L5.

Figure 27C:
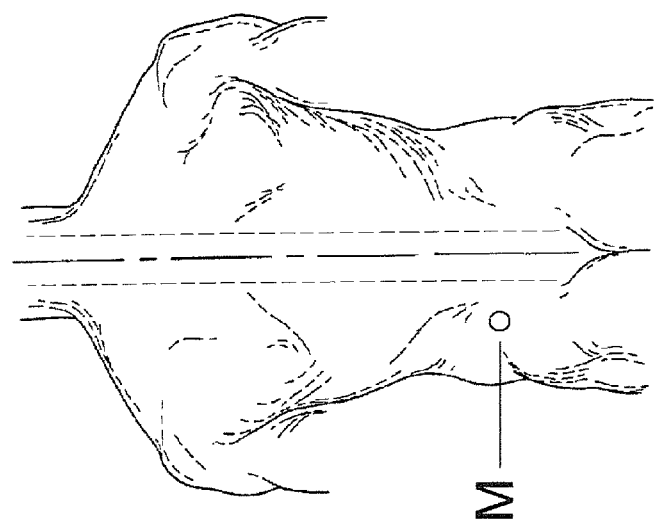

Another method of device implantation is shown in FIGS. 27C and 27O, which show a schematic illustration of the approximate location of incision site "M" and soft tissue corridor "N", which extends from incision "M" to the underlying interspinous space. In this method embodiment, an anterior column implant is placed using any known method for implant placement. These known methods include XUF (using corridor "O"), AUF, AXUF, GUF, or the like. The tissue corridor is not shown for each of these known procedures. In this method, corridor "N" is a postero-lateral approach to the inter-spinous space instead of the directly lateral approach (for example, corridor "Z") of FIG. 5. Otherwise, the method of device implantation is as already disclosed above and illustrated in FIGS. 19A through 27.

Figure 28A:
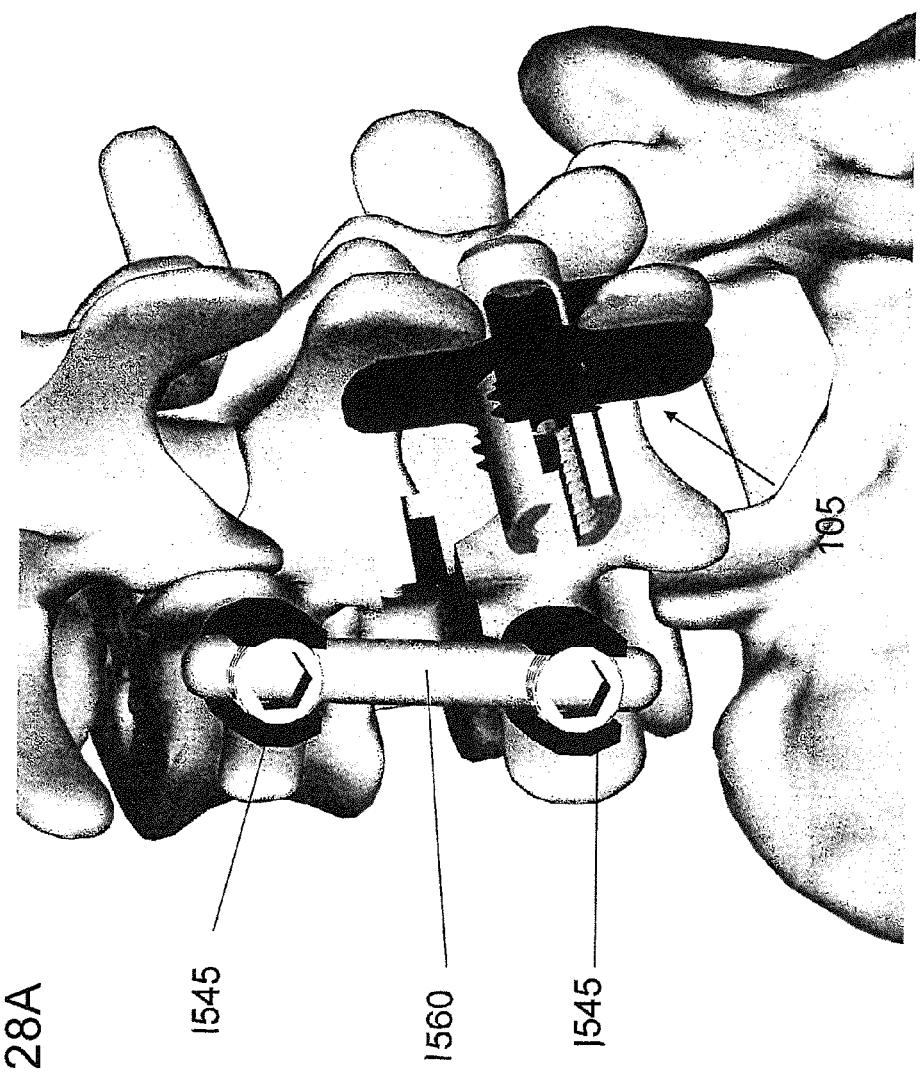
FIG. 28A illustrates use of the fixation device together with a bone fusion implant positioned into the pedicle portion near the anterior column.
Figure 28C:
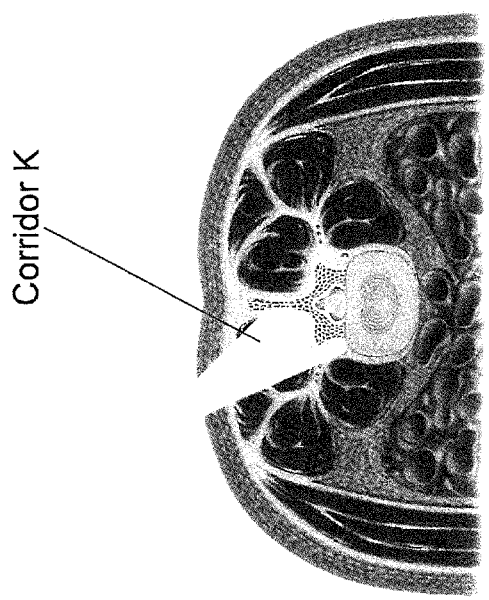
FIGS. 28B and 28C illustrate an alternative method of implant placement.
Figure 28B:
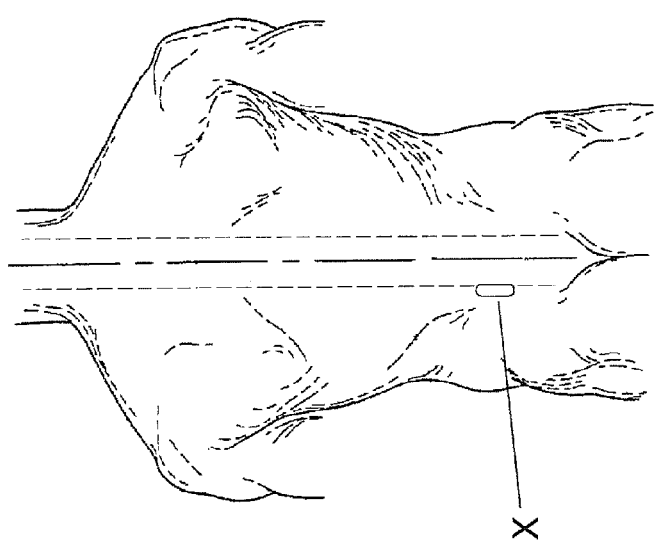

Another method is shown in FIG. 28A. In this embodiment, a portion of the facet joint is removed and a bone fusion implant is placed into the anterior column through the cavity created by the facet resection. This operation is known to those of ordinary skill in the art as a Trans-foraminal Lumbar Interbody Fusion (TLIF). A bone screw 1545 can be placed into the pedicle portion of bone at each of the upper (L4 level) and lower (L5 level) vertebral bones. A rod 1560 can be used to rigidly interconnect the screws 1545. The screws/rod can be placed on one side of the vertebral midline and a fixation device 105 as described above can be used to supplement the uni-lateral screw/rod fixation. In a preferred method of use, the implant 105 is implanted placed though the same (single) skin incision used to implant the screws 1545 and interconnecting rod 1560. FIGS. 28B and 28C show a schematic illustration of the approximate location of incision site "X" and soft tissue corridor "K", which extends from incision "X" to the underlying bone. In a first preferred embodiment, all implants are placed ipsilateral to the skin incision "X", wherein an implant 1546 is positioned into the disc space of the anterior column, two screws 1545 and an interconnecting rod 1560, as well as inter-spinous implant 105 are collectively delivered though corridor "K". There is no separate skin incision that is placed on the contralateral side of the spinous processes and no bone screws or other orthopedic implants are placed on the contralateral side of the spinous process through a separate contralateral skin incision.

In a second embodiment of device use, the method illustrated in FIG. 28A is used. However, a separate skin incision is made on the contralateral side of the spinous processes and bone screws or other orthopedic implants are placed on the contralateral side of the spinous process through a separate contralateral skin incision.

OTHER EMBODIMENTS

As described above, the fixation devices described herein as well as the components of the devices can vary in their geometry and configuration. For example, device 505 as shown in FIGS. 29A-29C can include rotation arms 580 and a plate member 520 having a "Z" configuration. In this embodiment, the rotation arms, advancing deployment member, locking nut and retention screw (similar to screw 220 of device 105) are substantially equivalent to the comparable components of device 105. Plate 520 differs from plate 120 in that the former has the "Z" configuration illustrated in FIGS.

29A-29C. Further, advancing deployment member is positioned in a rotated orientation relative to plate 520 so that the rotation arms 580, when rotationally deployed, can rest opposite each of the spike-bearing portions of plate 520 as shown in FIGS. 29A-C.

Figure 30A:
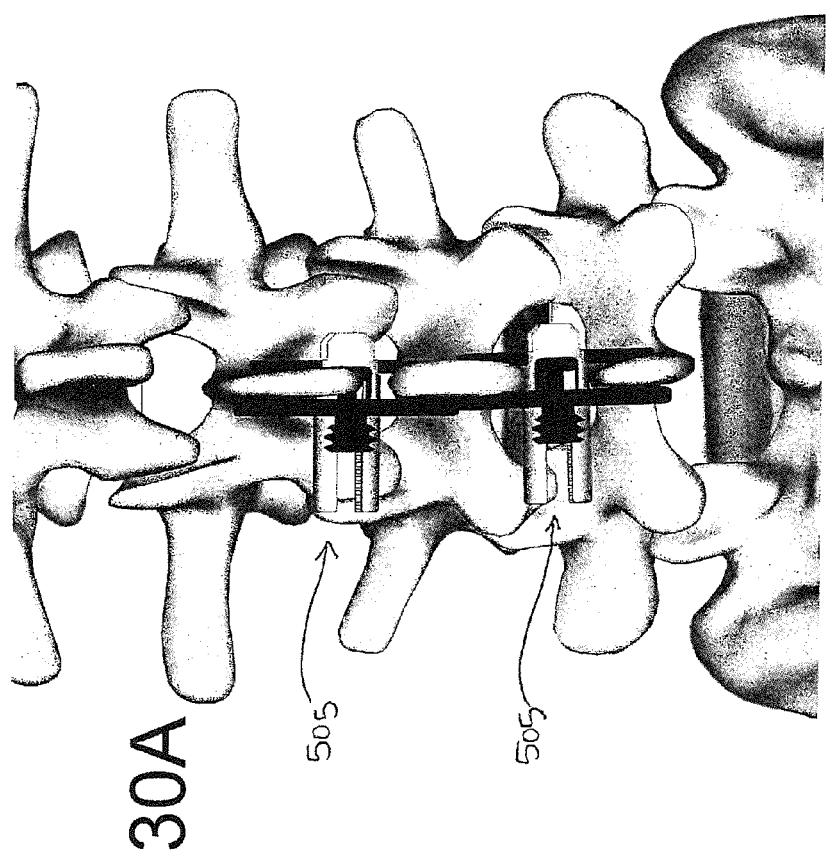
FIGS. 30A-30C illustrate the fixation device of FIGS. 29A-29C implanted between two adjacent functional spinal units.
Figure 30C:
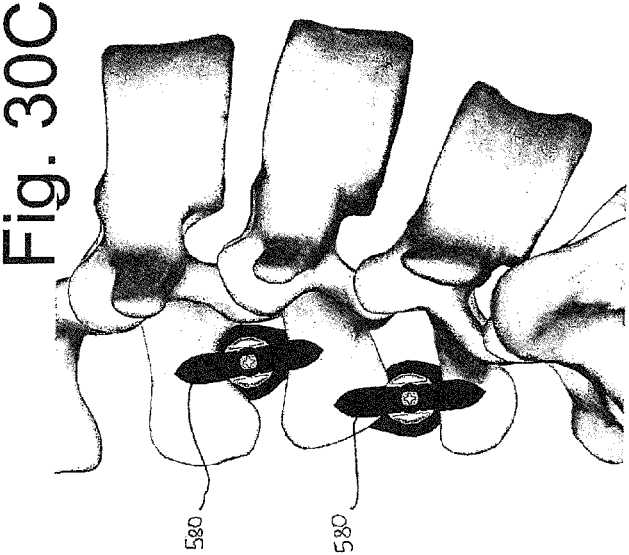
Figure 30B:
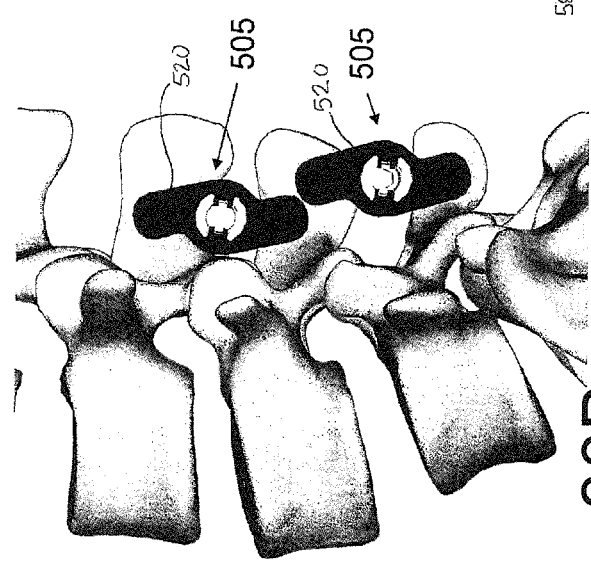

Device 505 permits the implantation of adjacent levels without interference from neighboring devices. FIGS. 30A-30C illustrate an implanted device 505 at each of two adjacent functional spinal units. The two implants 505 immobilize three adjacent vertebral bones. While an anterior column implant is not shown, it understood that the present invention contemplates placement of device 505 in conjunction with anterior column implants.

Figure 31A:
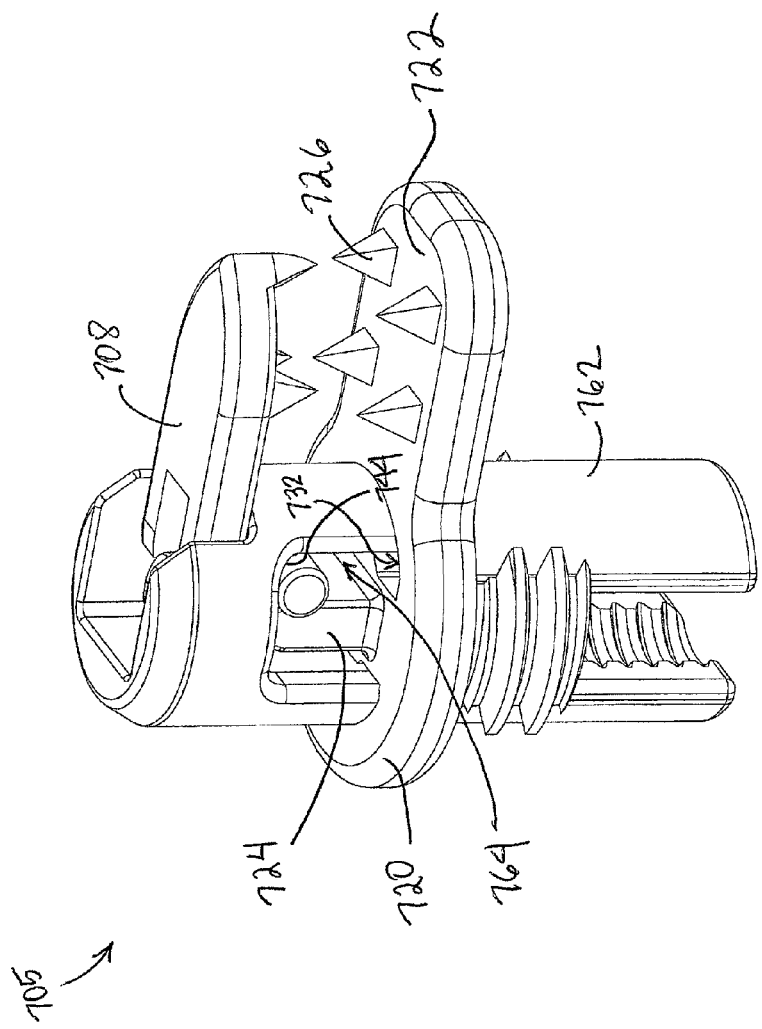

FIGS. 31A-31 E show another embodiment of a fixation device 705. In this embodiment, the plate member 720 includes a single bone-engaging surface 722 extending laterally to only one side of the central protrusion 724. Similarly, the device 705 has a single rotation arm 780 that translates through the member 750 as the screw 710 is rotated and draws elements 762 down through holes 732. As best shown in FIGS. 318-31 E, as the nut 710 threads with elements 762 and draws them down through holes 732, the central protrusion 724 having screw 721 inserted therethrough acts to urge the rotation arm 780 upwards through the bore of member 750. Hinge element 792 of rotation arm 780 abuts surface 744 of window 764. Rotation arm 780 begins to rotate around the axis of hinge element 792 from a perpendicular position relative to the plate member 720 until the bone-engaging surfaces 783, 722 of the rotation arm 780 and the plate member 720, respectively, are parallel to one another (see FIG. 31D). The nut 710 can be further rotated and the elements 762 drawn further through holes 732 such that bone-engaging surfaces 783, 722 of the rotation arm 780 and the plate member 720 are urged further translated towards one another until the bone of the spinous process engaged therebetween is compressed and penetrated by elements 726 and 782 (see FIG. 31 E).

Figure 32B:
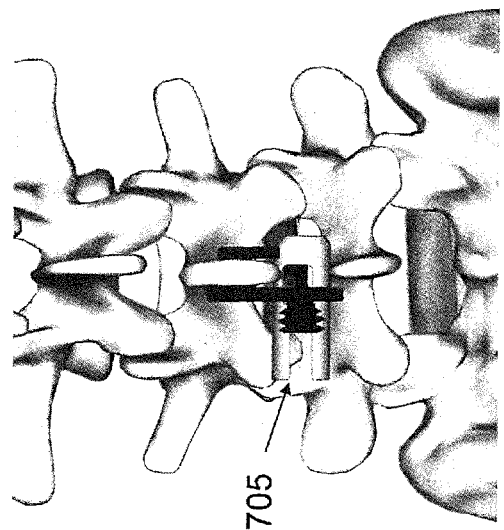
FIGS. 32A-32B illustrate the implanted device of FIGS. 31A-31 E.
Figure 32A:
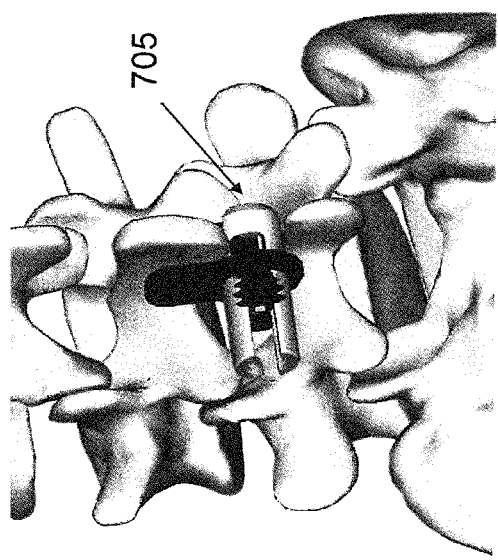

The embodiment of the FIGS. 31A-31 E is shown implanted onto a schematically represented spine in FIGS. 32A and 32B. In the present embodiment, member 762 is positioned in the inter-spinous space with the outer surface abutting the inferior aspect of the superior spinous process and the superior aspect of the inferior spinous process. Device 705 functions to limit vertebral extension and the extent to which the spinous processes can move towards one another at the implanted level. However, the implanted device 705 does not limit vertebral flexion or the extent of which the spinous processes may move away from one another. Unlike device 105 which is used to immobilize and fuse vertebral bone, device 705 is preferably used to maintain the relative movement between the vertebral bones but limit the extent of vertebral extension alone.

The disclosed devices or any of their components can be made of any biologically adaptable or compatible materials. Materials considered acceptable for biological implantation are well known and include, but are not limited to, stainless steel, titanium, tantalum, combination metallic alloys, various plastics (such as PEEK and the like), resins, ceramics, biologically absorbable materials and the like. Any components may be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the system or any of its components can also be entirely or partially made of a shape memory material or other deformable material.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A method for stabilizing a spinal segment comprising a superior vertebral bone, an immediately adjacent inferior vertebral bone and an intervening intervertebral disc space, said method comprising:
   identifying said spinal segment using an imaging modality;
   creating a first corridor configured to extend through a psoas muscle and onto a lateral side surface of said intervertebral disc space;
   advancing a first implant at least partially into said intervertebral disc space using said first corridor;
   advancing a second implant through a second corridor configured to extend onto a lateral aspect of an interspinous space positioned between a spinous process of said superior vertebral bone and a spinous process of said inferior vertebral bone, said second corridor being ipsilateral to said first corridor, and said second implant comprising:
      an elongated body configured to extend along a longitudinal axis from a proximal segment to a distal segment;
      a first bone abutment member configured to extend along a longitudinal axis from a proximal to a distal end and movably coupled to said distal segment of said elongated body; and
      a second bone abutment member configured to extend along a longitudinal axis from a proximal to a distal end and coupled to said proximal segment of said elongated body;
   advancing said second implant at least partially into said interspinous space, said first and said second bone abutment members of said second implant being positioned on opposing sides of at least one of said spinous process of said superior vertebral bone and/or said spinous process of said inferior vertebral bone;

performing a first actuation of a locking mechanism of said second implant, said first actuation thereof causing rotation of said longitudinal axis of said first bone abutment member to a greater angle with respect to said longitudinal axis of said elongated body;

performing a second actuation of said locking mechanism of said second implant, said second actuation thereof causing translation of said bone abutment members toward one another without further rotation of said first bone abutment member relative to said elongated body; and immobilizing said spinous process of said superior vertebral bone relative to said spinous process of said inferior vertebral bone.

2. The method of claim 1, wherein said act of advancing said first implant into said intervertebral disc space is performed through a first skin incision and said act of advancing said second implant onto said interspinous space is performed through a second skin incision.

3. The method of claim 2, wherein said first and said second skin incisions comprise separate but adjacent incisions.

4. The method of claim 1, wherein said second corridor is produced via placement of a surgical retractor assembly.

5. The method of claim 4, wherein said second corridor is produced via sequential addition of retractors of progressively greater diameter.

6. The method of claim 1, further comprising positioning bone forming material at least partially within said interspinous space.

7. The method of claim 1, wherein said first and said second corridors are accessed through said same skin incision.

8. The method of claim 1, wherein said first and said second corridors are substantially parallel.

9. The method of claim 1, wherein said act of advancing said first bone abutment member onto said first lateral side aspect of said spinous process is produced via actuation of a mechanism at least partially situated within said second implant.

10. The method of claim 1, wherein said first implant and/or said second implant is at least partially manufactured from a metallic alloy.

11. A method for fusion of a spinal segment comprising a superior vertebral bone, an immediately adjacent inferior vertebral bone and an intervening intervertebral disc space of a subject, said method comprising:

identifying said spinal segment on an imaging modality;

advancing a first implant into said intervertebral disc space using a first corridor within said subject that extends from a first lateral skin incision and onto a lateral side surface of said intervertebral disc space;

positioning said first implant within said intervertebral disc space through said first corridor;

advancing a second implant through a second corridor and onto a lateral aspect of an interspinous space, said interspinous space being positioned between a spinous process of said superior vertebral bone and a spinous process of said inferior vertebral bone, said second implant comprising:

an elongated body configured to extend along a longitudinal axis from a proximal segment to a distal segment;

a first bone abutment member configured to extend along a longitudinal axis from a proximal to a distal end and movably coupled to said distal segment of said elongated body; and a second bone abutment member configured to extend along a longitudinal axis from a proximal to a distal end and coupled to said proximal segment of said elongated body;

positioning said elongated body of said second implant at least partially within said interspinous space, said first bone abutment member being positioned on a side of said interspinous space contralateral to said first lateral skin incision, and said second bone abutment member being positioned on a side of said interspinous space ipsilateral to said first lateral skin incision;

actuating a mechanism of said second implant, said act of actuating advancing said first and said second bone abutment members towards one another; and immobilizing said spinous process of said superior vertebral bone relative to said spinous process of said inferior vertebral bone, wherein said locking mechanism of said second implant is further configured to:
(i) upon a first actuation thereof, cause rotation of said longitudinal axis of said first bone abutment member away from a parallel position relative to said longitudinal axis of said elongated body; and
(ii) upon a subsequent actuation thereof, cause translation of said bone abutment members toward one another without causing a further rotation of said first bone abutment member relative to said elongated body.

12. The method of claim 11, wherein:
said act of advancing said first implant into said intervertebral disc space is performed through said first lateral skin incision; and
said act of advancing said second implant onto said interspinous space is performed through a second skin incision.

13. The method of claim 12, wherein said first and said second skin incisions comprise separate incisions.

14. The method of claim 12, wherein said first and said second corridors are accessed through a same one of said first and second skin incisions.

15. The method of claim 11, wherein said second corridor is produced via placement of a surgical retractor assembly.

16. The method of claim 15, wherein said second corridor is produced via sequential addition of retractors of progressively greater diameter.

17. The method of claim 11, further comprising positioning bone forming material at least partially within said interspinous space and adjacent to said second implant.

18. The method of claim 11, wherein said act of advancing said first and said second bone abutment members towards one another further comprises causing a spinous process of said superior or inferior vertebral bone to be compressed therebetween.

19. The method of claim 11, wherein at least one of said first and second bone abutment members further comprises one or more features configured to potentiate implant anchor onto bone.

20. The method of claim 11, wherein at least said first actuation of said mechanism is further configured to be reversible.

21. The method of claim 11, wherein a locking instrument is used to actuate said mechanism.

22. The method of claim 11, wherein at least one of said first implant or said second implant is at least partially manufactured from a metallic alloy.

23. The method of claim 11, wherein at least one of said first implant or said second implant is at least partially manufactured from a plastic material.

24. A method for anterior and posterior decompression of a target spinal canal segment that is positioned between a superior vertebral bone and an inferior vertebral bone, said method comprising:
- identifying said target segment;
- placing a first implant within a disc space that is positioned between said superior vertebral bone and said inferior vertebral using a first corridor configured to extend from a posterior skin incision and through at least a portion of a facet joint that forms an articulation between said superior and inferior vertebral bones;
- advancing a second implant into an interspinous space between a spinous process of each of said superior and inferior vertebral bones, said second implant comprising:
  - an elongated body configured to extend along a longitudinal axis from a proximal segment to a distal segment;
  - a first bone abutment member configured to extend along a longitudinal axis from a proximal to a distal end and movably coupled to said distal segment of said elongated body; and
  - a second bone abutment member configured to extend along a longitudinal axis from a proximal to a distal end and coupled to said proximal segment of said elongated body;
- positioning said first and second bone abutment members of said second implant on opposing sides of at least one of said spinous processes of said superior and inferior vertebral bones;
- performing a first actuation of a locking mechanism of said second implant, said first actuation thereof causing rotation of said longitudinal axis of said first bone abutment member to a greater angle with respect to said longitudinal axis of said elongated body;
- performing a subsequent actuation of said locking mechanism of said second implant, said subsequent actuation thereof causing translation of said bone abutment members toward one another without further rotation of said first bone abutment member relative to said elongated body; and
- immobilizing said spinous process of said superior vertebral bone relative to said spinous process of said inferior vertebral bone.

25. The method of claim 24, wherein a locking instrument is used to actuate said locking mechanism and produce said first and second actuations.

26. The method of claim 25, wherein said locking mechanism is adapted to retain a compressive load placed onto at least one of said spinous processes of said superior and inferior vertebral bones after disengagement of said locking instrument from said locking mechanism.

27. The method of claim 24, further comprising anchoring a first bone screw into a pedicle of said superior vertebral bone, anchoring a second bone screw into pedicle of said inferior vertebral bone and connecting said first and second bone screws with a rod.

28. The method of claim 24, further comprising positioning bone fusion material at least partially within said interspinous space.

29. The method of claim 24, wherein said act of advancing said first implant into said intervertebral disc space and said act of advancing said second implant onto said interspinous space are performed through said posterior skin incision.

30. The method of claim 24, wherein said translation of said first and second bone abutment members towards one another causes at least one spinous process of said superior and inferior vertebral bones to be compressed therebetween.

31. The method of claim 24, wherein at least one of said first and second bone abutment members comprises one or more of features configured to potentiate implant anchor onto bone.

32. The method of claim 24, wherein a fourth bone abutment member is coupled to said distal segment of said elongated body, said first actuation of said locking mechanism concurrently rotating each of said first and fourth bone abutment members relative to said elongated body.

33. The method of claim 24, wherein at least said first actuation of said locking mechanism is further configured to be reversible.

34. The method of claim 24, wherein said first implant and/or said second implant is at least partially manufactured from a metallic alloy.

35. The method of claim 24, wherein said first implant and/or said second implant is at least partially manufactured from a plastic material.

36. A method for bony fusion of a first vertebral bone, an immediately adjacent second vertebral bone, and an intervening intervertebral disc space, said method comprising:
- identifying said first and second vertebral bones on an imaging modality;
- placing a skin incision posterior to a posterior aspect of a pedicle of an inferior one of said first and second vertebral bones;
- developing a first corridor to an ipsilateral facet joint from said incision, said facet joint comprising an articulation between said first and second vertebral bones;
- removing at least a portion of said facet joint;
- advancing at least a segment of a first implant into said intervertebral disc space through a trans-foraminal corridor;
- developing a second corridor to said lateral aspect of an inter-spinous space, said inter-spinous space being positioned between a spinous process of said first vertebral bone and a spinous process of said second vertebral bone;
- positioning a second implant within said interspinous space, said second implant comprising:
  - an elongated body configured to extend along a longitudinal axis from a proximal segment to a distal segment;
  - a first bone abutment member configured to extend along a longitudinal axis from a proximal to a distal end and movably coupled to said distal segment of said elongated body; and
  - a second bone abutment member configured to extend along a longitudinal axis from a proximal to a distal end and coupled to said proximal segment of said elongated body;
- positioning said elongated body of said second implant at least partially within said interspinous space, said first bone abutment member being positioned on a side of said interspinous space contralateral to said skin incision, and said second bone abutment member being positioned on a side of said interspinous space ipsilateral to said skin incision;
- actuating an advancement mechanism of said second implant to advance said first and said second bone abutment members towards one another; and immobilizing said spinous process of said first vertebral bone relative to said spinous process of said second vertebral bone,
wherein said advancement mechanism of said second implant is further configured to:
(i) upon a first actuation thereof, cause rotation of said longitudinal axis of said first bone abutment member away from a parallel position relative to said longitudinal axis of said elongated body; and
(ii) upon a subsequent actuation thereof, cause translation of said bone abutment members toward one another without causing a further rotation of said first bone abutment member relative to said elongated body.

37. The method of claim 36, further comprising:
anchoring a first bone screw into a pedicle of said first vertebral bone;
anchoring a second bone screw into a pedicle of said second vertebral bone; and
connecting said first and second bone screws via a rod.

38. The method of claim 36, further comprising positioning bone fusion material at least partially within said interspinous space.

39. The method of claim 36, wherein said act of advancing said first implant into said intervertebral disc space and said act of advancing said second implant onto said interspinous space are performed through said skin incision.

40. The method of claim 36, wherein said translation of said first and second bone abutment members towards one another causes at least one spinous process of said first and second vertebral bones to be compressed therebetween.

41. The method of claim 36, wherein at least one of said first and second bone abutment members comprises one or more of features configured to potentiate implant anchor onto bone.

42. The method of claim 36, wherein at least said first actuation of said advancement mechanism is further configured to be reversible.

43. The method of claim 36, wherein a locking instrument is used to actuate said advancement mechanism and produce said first and second actuations.

44. The method of claim 36, wherein at least one of said first implant or said second implant is at least partially manufactured from a metallic alloy.

45. The method of claim 36, wherein at least one of said first implant or said second implant is at least partially manufactured from a plastic material.

46. A method for bony fusion of a first vertebral bone, an immediately adjacent second vertebral bone, and an intervening intervertebral disc space, said method comprising:
identifying said first and second vertebral bones on an imaging modality;
placing a skin incision posterior to a posterior aspect of a pedicle of an inferior one of said first and second vertebral bones;
developing a first corridor to an ipsilateral facet joint from said incision, said facet joint comprising an articulation between said first and second vertebral bones;
removing at least a portion of said facet joint;
advancing at least a segment of a first implant into said intervertebral disc space through a trans-foraminal corridor;
developing a second corridor to said lateral aspect of an inter-spinous space, said inter-spinous space being positioned between a spinous process of said first vertebral bone and a spinous process of said second vertebral bone;
positioning a second implant within said interspinous space, said second implant comprising:
an elongated body configured to extend along a longitudinal axis from a proximal segment to a distal segment;
a first bone abutment member configured to extend along a longitudinal axis from a proximal to a distal end and movably coupled to said distal segment of said elongated body; and
a second bone abutment member configured to extend along a longitudinal axis from a proximal to a distal end and coupled to said proximal segment of said elongated body;
positioning said elongated body of said second implant at least partially within said interspinous space, said first bone abutment member being positioned on a side of said interspinous space contralateral to said skin incision, and said second bone abutment member being positioned on a side of said interspinous space ipsilateral to said skin incision;
actuating a locking mechanism of said second orthopedic implant to advance said first and said second bone abutment members towards one another; and
immobilizing said spinous process of said first vertebral bone relative to said spinous process of said second vertebral bone.

47. The method of claim 46, further comprising anchoring a first bone screw into a pedicle of said first vertebral bone, anchoring a second bone screw into a pedicle of said second vertebral bone and connecting said first and second bone screws via a rod.

48. The method of claim 46, further comprising positioning bone fusion material at least partially within said interspinous space.

49. The method of claim 46, wherein said act of advancing said first implant into said intervertebral disc and said act of advancing said second implant onto said interspinous space are performed through said skin incision.

50. The method of claim 46, wherein said translation of said first and second bone abutment members towards one another causes at least one spinous process of said first and second vertebral bones to be compressed therebetween.

51. The method of claim 46, wherein at least one of said first and second bone abutment members comprises one or more of features configured to potentiate implant anchor onto bone.

* * * * *